(12) United States Patent
Swann et al.

(10) Patent No.: US 8,235,047 B2
(45) Date of Patent: Aug. 7, 2012

(54) METHODS AND DEVICES FOR DEPLOYMENT INTO A LUMEN

(75) Inventors: Betsy Swann, Grass Valley, CA (US); Dai Ton, Milpitas, CA (US); Ashish Khera, Maplewood, NJ (US)

(73) Assignee: Conceptus, Inc., Mountain View, CA (US)

( * ) Notice: Subject to any disclaimer, the term of this patent is extended or adjusted under 35 U.S.C. 154(b) by 980 days.

(21) Appl. No.: 11/396,209

(22) Filed: Mar. 30, 2006

(65) Prior Publication Data

US 2007/0227544 A1    Oct. 4, 2007

(51) Int. Cl.
  *A61F 6/06* (2006.01)
  *A61F 6/14* (2006.01)
  *A61F 13/00* (2006.01)
  *A61F 2/00* (2006.01)
  *A61B 17/08* (2006.01)
  *A61M 29/00* (2006.01)

(52) U.S. Cl. ........ 128/831; 128/830; 128/832; 128/833; 128/839; 128/840; 128/843; 606/151; 606/191; 606/200; 424/422; 424/423; 424/424; 424/425; 424/432

(58) Field of Classification Search .......... 128/830–833, 128/839–840, 843; 606/159, 200, 151, 191; 424/422–425, 432
See application file for complete search history.

(56) References Cited

U.S. PATENT DOCUMENTS

| | | | |
|---|---|---|---|
| 3,334,629 A * | 8/1967 | Cohn | ............................ 606/194 |
| 3,625,214 A | 12/1971 | Higuchi | |
| 3,687,129 A | 8/1972 | Nuwayser | |
| 3,815,578 A | 6/1974 | Bucalo | |
| 3,855,996 A | 12/1974 | Bolduc | |
| 3,865,108 A | 2/1975 | Hartop | |
| 3,868,956 A | 3/1975 | Alfidi et al. | |
| 3,952,747 A * | 4/1976 | Kimmell, Jr. | ................. 606/195 |
| 3,991,750 A | 11/1976 | Vickery | |
| 3,991,760 A | 11/1976 | Drobish et al. | |
| 4,052,754 A | 10/1977 | Homsy | |
| 4,140,126 A | 2/1979 | Choudhury | |
| 4,185,618 A | 1/1980 | Corey | |
| 4,246,896 A | 1/1981 | Horne et al. | |
| 4,279,252 A | 7/1981 | Martin | |
| 4,503,569 A | 3/1985 | Dotter | |
| 4,562,596 A | 1/1986 | Kornberg | |

(Continued)

FOREIGN PATENT DOCUMENTS

AU    707047    7/1999

(Continued)

OTHER PUBLICATIONS

PCT International Search Report and Written Opinion for PCT/US2007/005400, Int'l. filing date Feb. 28, 2007, mailed Aug. 11, 2007, 21 pages.

(Continued)

*Primary Examiner* — Patricia Bianco
*Assistant Examiner* — Brandon Jackson
(74) *Attorney, Agent, or Firm* — Blakely, Sokoloff, Taylor & Zafman LLP

(57) ABSTRACT

The invention described is directed to an intracorporeal occluding device having elements with non-traumatic ends and devices, systems and methods for occluding the lumens of anatomical passageways and/or for delivering drugs or other substances to the bodies of human or animal subjects.

24 Claims, 30 Drawing Sheets

U.S. PATENT DOCUMENTS

| | | | |
|---|---|---|---|
| 4,577,631 A | 3/1986 | Kreamer | |
| 4,579,110 A | 4/1986 | Hamou | |
| 4,585,000 A | 4/1986 | Hershenson | |
| 4,595,000 A | 6/1986 | Hamou | |
| 4,606,336 A | 8/1986 | Zeluff | |
| 4,638,803 A | 1/1987 | Rand | |
| 4,643,184 A * | 2/1987 | Mobin-Uddin | 606/200 |
| 4,657,000 A | 4/1987 | Hepburn | |
| 4,688,553 A * | 8/1987 | Metals | 128/899 |
| 4,700,701 A | 10/1987 | Montaldi | |
| 4,733,665 A | 3/1988 | Palmaz | |
| 4,787,899 A | 11/1988 | Lazarus | |
| 4,869,268 A | 9/1989 | Yuon | |
| 4,964,850 A | 10/1990 | Boulton et al. | |
| 4,969,458 A | 11/1990 | Wiktor | |
| 4,990,156 A * | 2/1991 | Lefebvre | 606/200 |
| 4,994,069 A | 2/1991 | Ritchart et al. | |
| 5,024,671 A | 6/1991 | Tu et al. | |
| 5,104,399 A | 4/1992 | Lazarus | |
| 5,108,420 A | 4/1992 | Marks | |
| 5,147,370 A | 9/1992 | McNamara et al. | |
| 5,152,777 A | 10/1992 | Goldberg et al. | |
| 5,163,958 A | 11/1992 | Pinchuk | |
| 5,167,614 A | 12/1992 | Tessmann et al. | |
| 5,176,692 A | 1/1993 | Wilk et al. | |
| 5,190,546 A | 3/1993 | Jervis | |
| 5,192,301 A | 3/1993 | Kamiya et al. | |
| 5,197,978 A | 3/1993 | Hess | |
| 5,226,911 A | 7/1993 | Chee et al. | |
| 5,256,146 A | 10/1993 | Ensminger et al. | |
| 5,267,945 A | 12/1993 | Doctor et al. | |
| 5,275,622 A | 1/1994 | Lazarus et al. | |
| 5,303,719 A | 4/1994 | Wilk et al. | |
| 5,304,194 A | 4/1994 | Chee et al. | |
| 5,324,304 A * | 6/1994 | Rasmussen | 606/200 |
| 5,344,427 A * | 9/1994 | Cottenceau et al. | 606/200 |
| 5,354,295 A | 10/1994 | Guglielmi et al. | |
| 5,366,472 A | 11/1994 | Hillstead | |
| 5,370,657 A | 12/1994 | Irie | |
| 5,382,259 A | 1/1995 | Phelps et al. | |
| 5,382,261 A | 1/1995 | Palmaz | |
| 5,423,849 A | 6/1995 | Engelson et al. | |
| 5,433,217 A | 7/1995 | Pianetti et al. | |
| 5,433,218 A | 7/1995 | Wildemeersch | |
| 5,443,500 A | 8/1995 | Sigwart | |
| 5,456,713 A | 10/1995 | Chuter | |
| 5,474,089 A | 12/1995 | Waynant | |
| 5,489,295 A | 2/1996 | Piplani et al. | |
| 5,499,995 A | 3/1996 | Teirstein | |
| 5,507,811 A | 4/1996 | Koike et al. | |
| 5,512,051 A | 4/1996 | Wang et al. | |
| 5,514,176 A | 5/1996 | Bosley | |
| 5,522,822 A | 6/1996 | Phelps et al. | |
| 5,545,210 A | 8/1996 | Hess et al. | |
| 5,582,619 A | 12/1996 | Ken | |
| 5,601,593 A | 2/1997 | Freitag | |
| 5,601,595 A | 2/1997 | Smith | |
| 5,601,600 A | 2/1997 | Ton | |
| 5,634,942 A | 6/1997 | Chevillon et al. | |
| 5,643,311 A | 7/1997 | Smith et al. | |
| 5,656,036 A | 8/1997 | Palmaz | |
| 5,669,933 A * | 9/1997 | Simon et al. | 600/200 |
| 5,693,067 A | 12/1997 | Purdy | |
| 5,704,910 A | 1/1998 | Humes | |
| 5,766,203 A | 6/1998 | Imran et al. | |
| 5,792,154 A | 8/1998 | Doan et al. | |
| 5,836,968 A | 11/1998 | Simon et al. | |
| 5,855,915 A | 1/1999 | Pinkus | |
| 5,919,202 A | 7/1999 | Yoon et al. | |
| 5,935,137 A | 8/1999 | Saadat et al. | |
| 5,979,446 A | 11/1999 | Loy | |
| 5,980,554 A | 11/1999 | Lenker et al. | |
| 6,090,063 A | 7/2000 | Makower et al. | |
| 6,096,052 A | 8/2000 | Callister et al. | |
| 6,099,562 A | 8/2000 | Ding et al. | |
| 6,145,505 A | 11/2000 | Nikolchev et al. | |
| 6,174,322 B1 | 1/2001 | Schneidt | |
| 6,176,240 B1 | 1/2001 | Nikolchev et al. | |
| 6,187,027 B1 | 2/2001 | Mariant et al. | |
| 6,231,589 B1 * | 5/2001 | Wessman et al. | 606/200 |
| 6,251,122 B1 | 6/2001 | Tsukernik | |
| 6,267,776 B1 * | 7/2001 | O'Connell | 606/200 |
| 6,270,495 B1 | 8/2001 | Palermo | |
| 6,273,901 B1 | 8/2001 | Whitcher et al. | |
| 6,306,914 B1 | 10/2001 | de Ziegler et al. | |
| 6,368,338 B1 | 4/2002 | Konya et al. | |
| 6,378,524 B1 | 4/2002 | Jones | |
| 6,432,116 B1 | 8/2002 | Callister et al. | |
| 6,436,120 B1 * | 8/2002 | Meglin | 606/200 |
| 6,468,290 B1 * | 10/2002 | Weldon et al. | 606/200 |
| 6,517,559 B1 * | 2/2003 | O'Connell | 606/158 |
| 6,526,979 B1 | 3/2003 | Nikolchev et al. | |
| 6,589,266 B2 * | 7/2003 | Whitcher et al. | 606/200 |
| 6,634,361 B1 | 10/2003 | Nikolchev et al. | |
| 6,679,266 B2 | 1/2004 | Nikolchev et al. | |
| 6,684,884 B2 | 2/2004 | Nikolchev et al. | |
| 6,705,323 B1 | 3/2004 | Nikolchev et al. | |
| 6,706,054 B2 | 3/2004 | Wessman et al. | |
| 6,708,056 B2 * | 3/2004 | Duchon et al. | 600/431 |
| 6,709,667 B1 * | 3/2004 | Lowe et al. | 424/422 |
| 6,763,833 B1 | 7/2004 | Khera et al. | |
| 6,782,217 B1 * | 8/2004 | Ando | 399/79 |
| 6,939,569 B1 | 9/2005 | Green et al. | 424/667 |
| 7,041,117 B2 * | 5/2006 | Suon et al. | 606/200 |
| 7,073,504 B2 | 7/2006 | Callister et al. | |
| 7,094,249 B1 * | 8/2006 | Broome et al. | 606/200 |
| 7,506,650 B2 * | 3/2009 | Lowe et al. | 128/830 |
| 7,694,683 B2 * | 4/2010 | Callister et al. | 128/831 |
| 2002/0020417 A1 * | 2/2002 | Nikolchev et al. | 128/831 |
| 2002/0029051 A1 | 3/2002 | Callister | |
| 2002/0147462 A1 | 10/2002 | Mair et al. | |
| 2003/0066533 A1 | 4/2003 | Loy | |
| 2004/0079377 A1 | 4/2004 | Nikolchev et al. | |
| 2004/0127918 A1 | 7/2004 | Nikolchev et al. | |
| 2004/0159324 A1 | 8/2004 | Nikolchev et al. | |
| 2004/0163650 A1 * | 8/2004 | Lowe et al. | 128/830 |
| 2004/0163651 A1 | 8/2004 | Nikolchev et al. | |
| 2004/0206358 A1 | 10/2004 | Nikolchev et al. | |
| 2004/0211429 A1 | 10/2004 | Nikolchev et al. | |
| 2005/0045183 A1 * | 3/2005 | Callister et al. | 128/831 |
| 2005/0085844 A1 * | 4/2005 | Tremulis et al. | 606/193 |
| 2007/0056591 A1 | 3/2007 | McSwain | |

FOREIGN PATENT DOCUMENTS

| | | |
|---|---|---|
| AU | 739429 | 10/2001 |
| CN | 87201529 U | 2/1988 |
| CN | 2211818 Y | 11/1995 |
| CN | 1251510 A | 4/2000 |
| CN | 2418852 Y | 2/2001 |
| DE | 30 38 928 A1 | 4/1982 |
| EP | 0 105 669 | 4/1984 |
| EP | 0 882 428 A2 | 12/1998 |
| EP | 0 199 049 | 4/2002 |
| EP | 1 295 563 A1 | 3/2003 |
| EP | 1 433 437 A2 | 6/2004 |
| EP | 1 459 707 A1 | 9/2004 |
| JP | 04-501966 A | 4/1992 |
| JP | 08-033665 A | 2/1996 |
| JP | A-2001-517484 | 10/2001 |
| WO | WO 90/09158 | 8/1990 |
| WO | WO 93/06884 | 4/1993 |
| WO | WO 94/24944 | 11/1994 |
| WO | WO 94/26175 | 11/1994 |
| WO | WO 96/40024 | 12/1996 |
| WO | WO 97/27893 | 8/1997 |
| WO | WO 98/26737 | 6/1998 |
| WO | WO 99/15116 | 4/1999 |
| WO | WO 01/13833 | 3/2001 |
| WO | WO 01/30267 | 5/2001 |
| WO | WO 02/15962 A2 | 2/2002 |
| WO | WO 02/071977 A2 | 9/2002 |
| WO | WO 2004/058109 | 7/2004 |
| WO | WO 2004/058110 | 7/2004 |
| WO | WO 2004/082532 A1 | 9/2004 |
| WO | WO 2005/000161 A2 | 1/2005 |
| WO | WO 2005/105008 A2 | 11/2005 |

OTHER PUBLICATIONS

PCT Notification of Invitation to Pay Additional Fees, PCT/US2007/005400, mailed on Aug. 3, 2007 (7 Pages).
PCT Notification Concerning Transmittal of International Preliminary Report on Patentability (Chapter of the Patent Cooperation Treaty);and Written Opinion for PCT/US2007/005400, International filing date Feb. 28, 2007, mailed Oct. 9, 2008, 7 ((2-sided) pages.
PCT International Search Report for PCT/US03/41341 (P049PCT1), mailed Sep. 7, 2004, 10 pages.
PCT International Search Report for PCT/US03/41275 (P049PCT2), mailed Jun. 8, 2004, 8 pages.
PCT Written Opinion of the International Searching Authority for PCT/US03/41275 (P049PCT2), mailed Apr. 25, 2005, 4 pages.
PCT International Search Report for PCT/US2005/003185 (P052PCT), mailed May 2, 2005, 8 pages.
PCT Written Opinion of the International Searching Authority for PCT/US05/003185, mailed May 2, 2005, 3 pages.
PCT International Search Report for PCT/US2005/003310 (P050PCT), mailed May 2, 2005, 9 pages.
PCT Written Opinion of the International Searching Authority for PCT/US2005/003310, mailed May 2, 2005, 5 pages.
PCT International Search Report and Written Opinion for PCT/US04/20976 (P047XPCT), mailed Sep. 1, 2005, 12 pages.
PCT International Preliminary Report on Patentability for PCT/US04/20976 (P047XPCT), issued Jan. 3, 2006, 7 pages.
PCT International Preliminary Report on Patentability, for PCT/US03/41275 (P049PCT2), mailed Sep. 22, 2005, (4 pages).
T. Schmitz-Rode, MD, et al., "Experimental nonsurgical female sterilization: transcervical implantation of microspindles in fallopian tubes," Journal of Vascular and Interventional Radiology, vol. 5, No. 6, pp. 905-910, (Nov.-Dec. 1994).
T. Schmitz-Rode, MD, et al., "Self-expandable spindle for transcatheter vascular occlusion: in vivo experiments," Radiology, vol. 188 No. 1, pp. 95-100, (Jul. 1993).
A. Thurmond, MD, "Transcervical fallopian tube catheterization," Seminars in Interventional Radiology, vol. 9. No. 2, pp. 80-86, (Jun. 1992).
European Patent Application No. 04777301.5, Supplementary European Search Report Dated Oct. 20, 2010, 6 pages.
St. Croix, et al., Brad "Genes Expressed in Human Tumor Endothelium," Science Magazine Aug. 18, 2000: vol. 289. No. 5482, pp. 1197-1202.

* cited by examiner

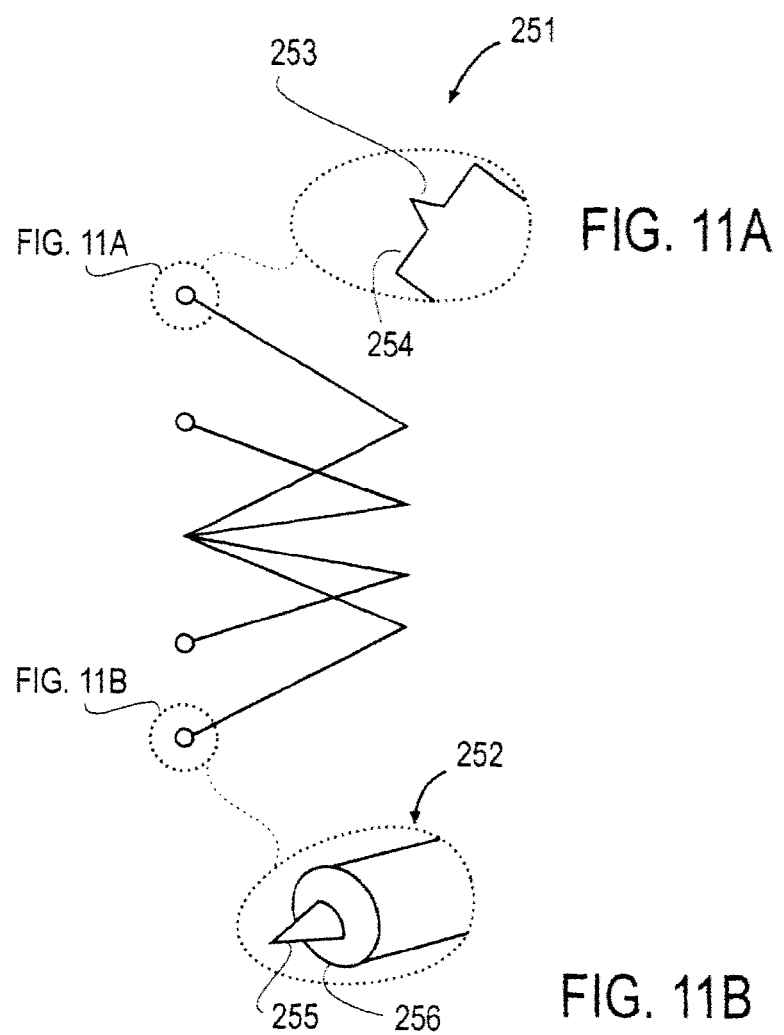

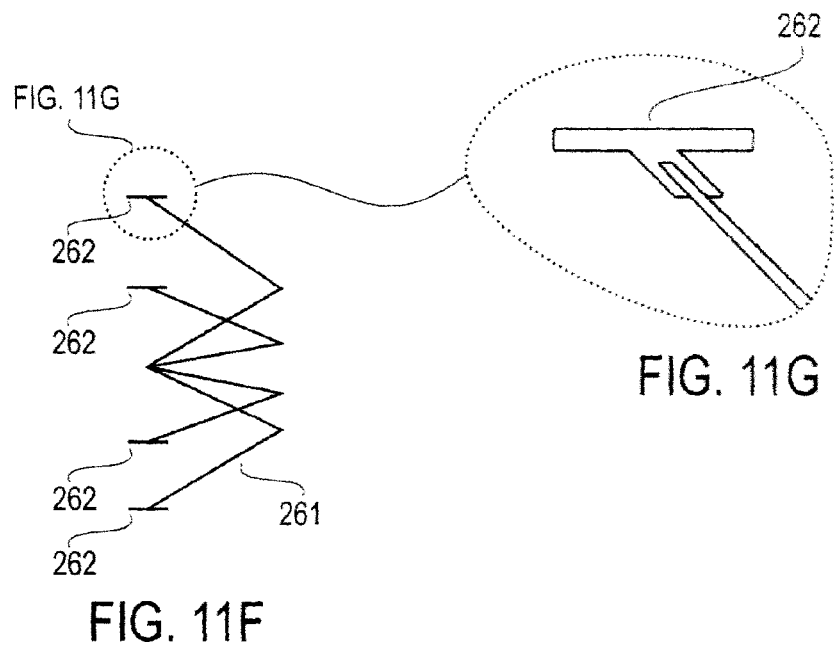
FIG. 11F
FIG. 11G
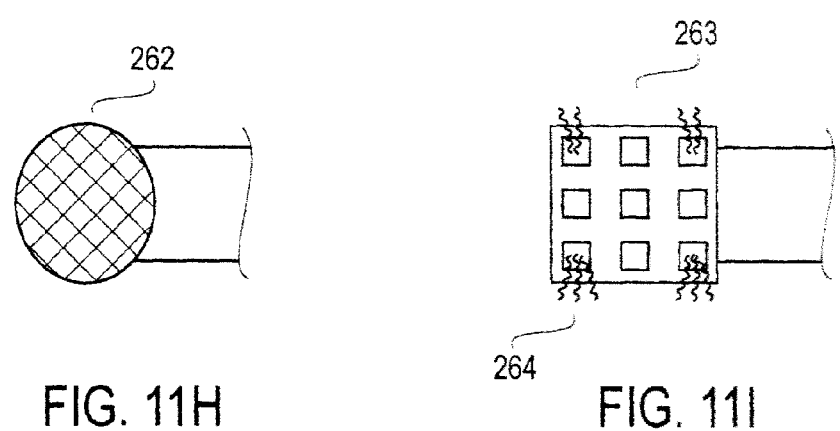
FIG. 11H
FIG. 11I

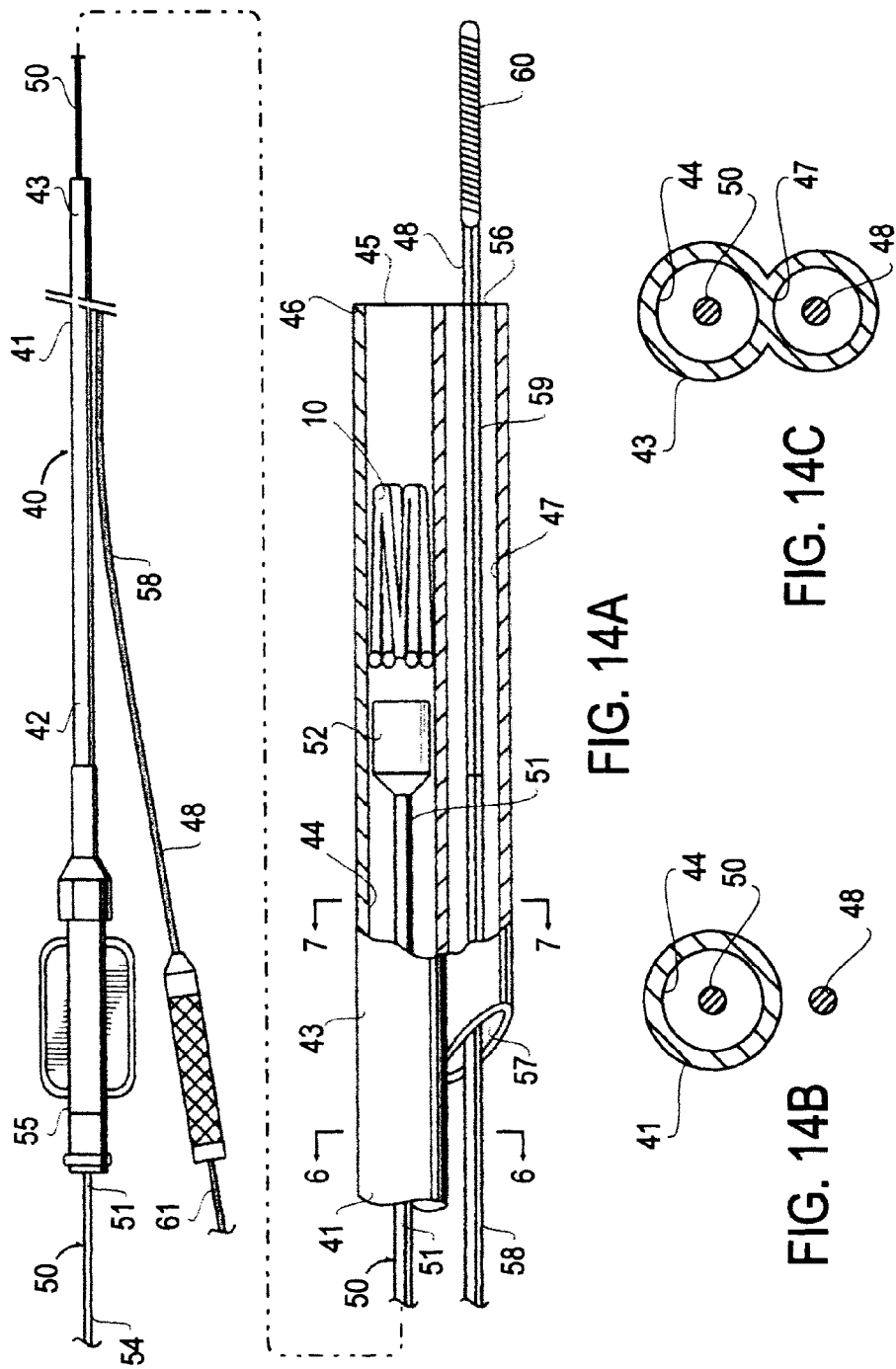

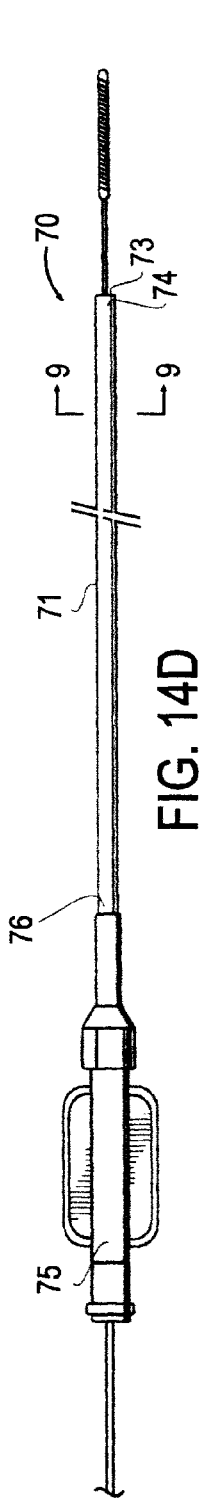
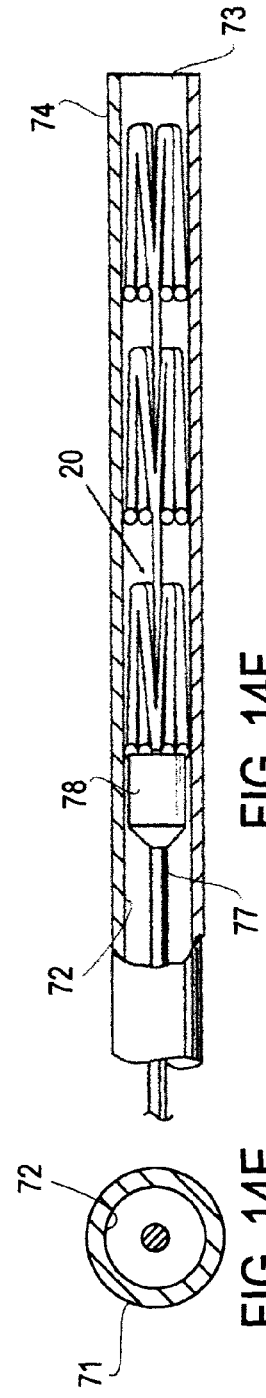
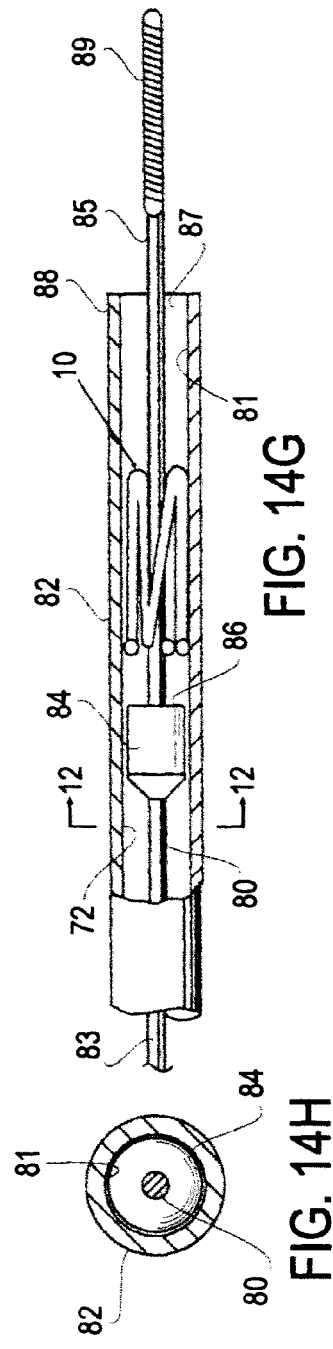
FIG. 14D
FIG. 14E
FIG. 14F
FIG. 14G
FIG. 14H

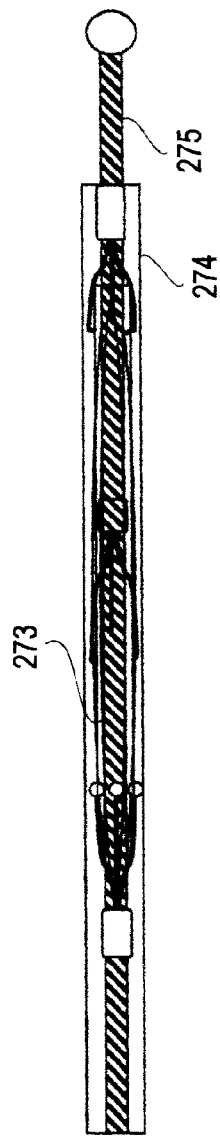
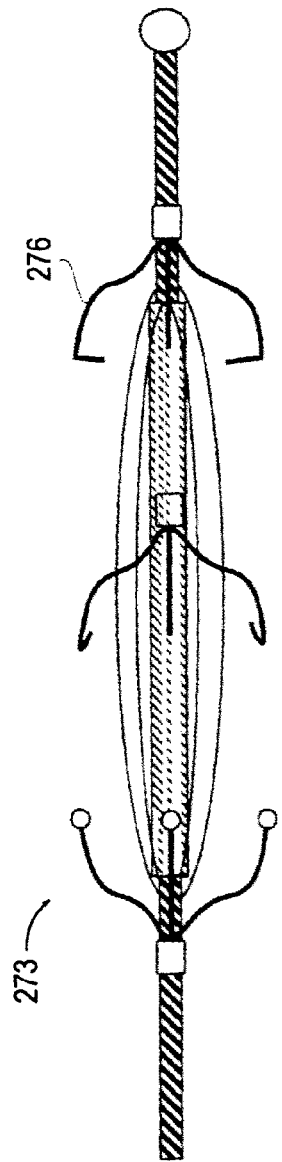
FIG. 16A
FIG. 16B

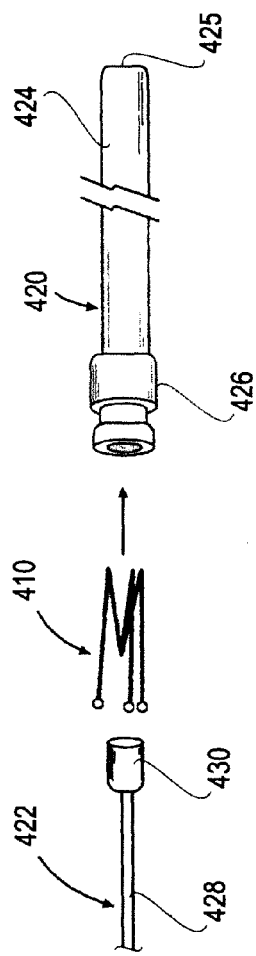
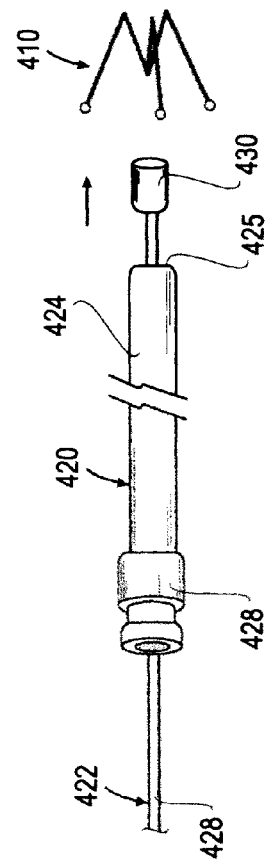
FIG. 18A
FIG. 18B

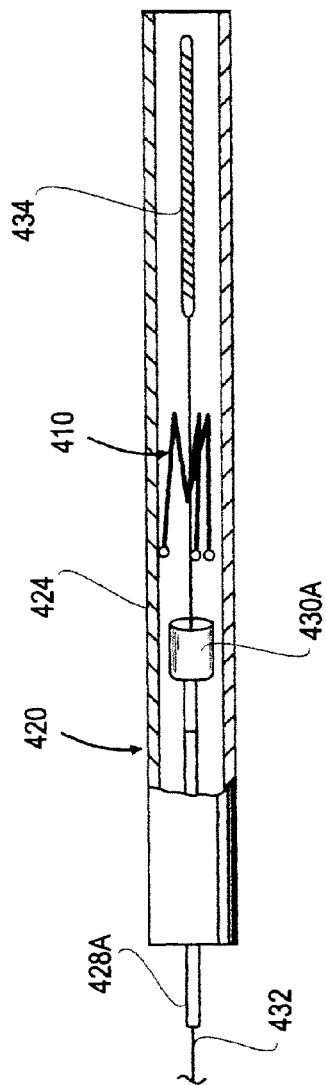
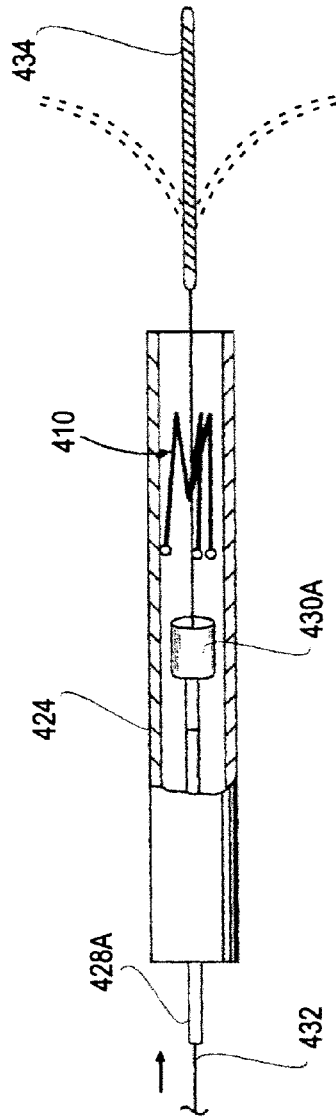
FIG. 19A
FIG. 19B

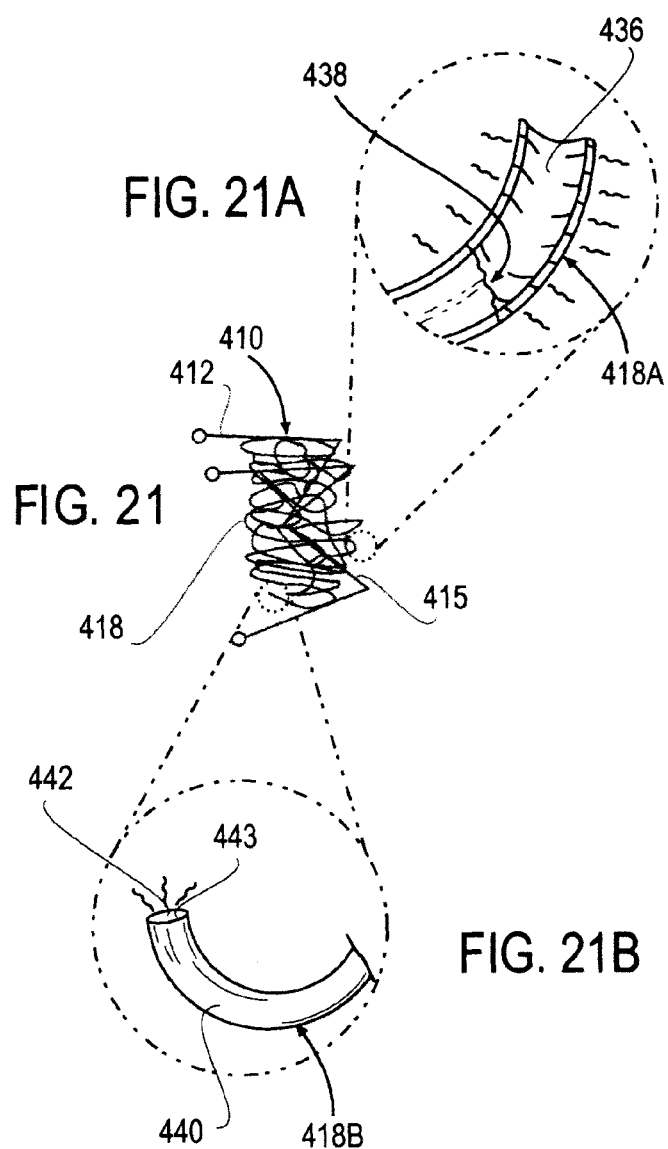

METHODS AND DEVICES FOR DEPLOYMENT INTO A LUMEN

BACKGROUND OF THE INVENTION

This invention generally relates to the field of occluding devices, delivery systems for such devices and methods of using such devices and systems in the occlusion of body passageways. The invention is particularly useful for occluding reproductive lumens such as a female patient's fallopian tubes or a male patient's vas deferens to affect contraception. Although the occlusion of a patient's reproductive lumens will be discussed herein in detail, it can be appreciated that the devices, methods and systems described herein can easily be adapted to occlude a patient's arteries or veins in a variety of situations. the nidus of an arterial-venous malformation, patent ductus arteriosis in infants, as well as feeding arteries to cancerous tumors, among other passageways. The invention also provides means for delivering vessel supporting devices such as coronary stents or venous or arterial embolic filters, to the desired location through a steerable system. Those skilled in the art will immediately recognize that various combinations, modifications, and equivalents of the inventions described herein can be used without departing from the scope of these inventions.

Conventional contraceptive strate gies generally fall within three categories: physical barriers, drugs and surgery. While each have certain advantages, they also suffer from various drawbacks. Barriers such as condoms and diaphragms are subject to failure due to breakage, displacement and misplacement. Drug strategies, such as the pill and Norplant.™, which rely on artificially controlling hormone levels, suffer from known and unknown side-effects from prolonged use. Surgical procedures, such as tubal ligation and vasectomy, are very effective, but involve the costs and attendant risks of surgery, and are frequently not reversible.

There exist various situations in which it is desirable to implant embolic or occlusive devices within lumens or anatomical passageways within the bodies of human or animal subjects. In at least some of those situations, it is additionally desirable to deliver a substance (e.g., a drug, a protein, cells, a biological material, a chemical substance, a gene therapy preparations, etc.) for at least an initial period of time following implantation of the embolic or occlusive device.

For example, it has been known to implant occlusive devices into the fallopian tubes of females or the vas deferens of males for contraceptive purposes. Examples of implantable occlusive devices useable for such purposes are described in U.S. Pat. No. 6,096,052 (Callister et al.) entitled Occluding Device and Method of Use and U.S. Pat. No. 6,432,116 (Callister et al.) entitled Occluding Device and Method of Use, the entireties of both such United States patents being expressly incorporated herein by reference. Some of these devices have been constructed and/or implanted in a manner to facilitate tissue ingrowth subsequent to implantation of the device such that, after such tissue ingrowth has occurred, the ingrown tissue alone or in combination with the implanted device will provide complete occlusion of the lumen of the fallopian tube or vas deferens. Thus, during the period between implantation of the device and completion of the lumen-occluding tissue ingrowth, the lumen of the fallopian tube or vas deferens may remain at least partially open. Thus, it may be desirable to provide alternative contraceptive means to prevent unwanted pregnancy during the period between implantation of the device and completion of the lumen-occluding tissue ingrowth.

The above incorporated U.S. patent application Ser. No. 08/770,123 (Callister et al.) described various embodiments of lumen occluding devices that may be used to occlude the lumen of a fallopian tube or vas deferens, some of which may deliver a drug, such as a contraceptive agent.

The fallopian tubes tend to exude objects through peristaltic (muscular contraction) and ciliated forces, and the direction of the force varies with menstrual cycle. These forces may result in the displacement of an implant. Past implant designs have been designed to counteract these forces, examples of which are found in U.S. patent applications Ser. No. 10/880,355, and Ser. No. 10/746,131, which are hereby incorporated by reference. However these designs may result in the puncture of the fallopian tube wall because they have unprotected free ends. Therefore it is desirable to incorporate a design which counteracts the forces in the fallopian tube while not completely puncturing the tube walls.

SUMMARY OF THE INVENTION

The present invention is directed to occlusion devices, delivery systems for such devices and methods of using such devices and systems for occluding body passageways particularly reproductive body lumens such as a female's fallopian tubes and a male's vas deferens.

The occlusion device embodying features of the invention has at least one segment with a plurality of expansive elements, preferably self-expanding, secured by one end thereof to a central location within the device. The first segment has a first expansive element with a first secured end and a second free end radially spaced from the first end when in an expanded configuration. The first segment preferably has at least one additional expansive element having a first secured end and a second non-traumatic end radially spaced from the first end in the expanded configuration. Preferably expansive elements are equally spaced about the central location of each segment with the first secured ends of the expansive elements being secured at the central location.

The non-traumatic end may be ball-shaped, contoured wire, or a pad. Examples of contoured wire include coils, sharp bends, large radius bends. The non-traumatic ends may have small features which hold into the tissue with out completely puncturing it, such as a spike. The non-traumatic ends may also be textured in encourage tissue growth. A non-traumatic end may be in the form of a pad. The pad may be textured, and may have pockets. The pockets may be filled with fibers to encourage tissue growth, or drugs as listed below.

The occlusion member may have one or more self expanding expansive spider-like segments (hereinafter spider segments). A plurality of spider segments are preferably axially aligned and secured together by connecting members. Specifically, the occluding member may have a first spider segment at a first end of the device, a second spider segment at a second end of the device. In further embodiments, the occluding device may have at least one intermediate spider segment between the first and second spider segments. The self expansive spider devices are preferably secured together by connecting members such as straight beams or curvilinear structures such as S-shape or Z-shape members. Connecting members having other shapes may also be employed.

The expansive elements of the spider segments may have a first section extending from the first end of the element which is oriented toward a first end of the occluding member and a second section extending to the second end of the expansive element which is oriented to a second end of the occluding member. The sections of the expansive elements may be straight or curved or have other shapes. The orientation of the expansive elements may alternate so that the first section of one expansive element of a spider segment is oriented in a first direction toward one end of the device and the first section of another expansive element of the same spider segment is oriented in a second direction toward a second end of the device. Additionally, the second section of a first expansive element may be oriented toward the second end of the occluding member and the second section of a second expansive element is oriented toward a second end of the occluding member. Alternatively, the expansive elements of one spider segment may be oriented in one direction and the expansive elements of another spider element may be in a second, (e.g. opposite) direction. The angle between the first and second sections of the expansive elements may be varied to allow for sizing the expanded configuration of the occluding device.

The occluding device may be delivered to an intracorporeal location through a delivery system which has a delivery catheter with an inner lumen configured to receive the occluding device in a constricted configuration, where the expansive elements of the one or more spider segments of the occluding device are radially compressed. A pusher element is slidably disposed within the inner lumen of the delivery catheter and has a distal end or head configured to engage the proximal end of the constricted occluding device and urge the occluding device out a discharge port in the distal end of the catheter. The pusher element is configured so that the proximal end thereof will extend out of the patient when deploying the occluding device to facilitate the manipulation of the pusher element. Because the occluding device is capable of being compressed to a very low profile, the delivery catheter may be restricted to very small transverse dimensions. Suitable delivery catheters may have an inner diameter of about 0.008 to about 0.08 inch (0.2-2.00 mm), preferably about 0.015 to about 0.025 inch (0.4-0.6 mm). The smaller diameter delivery catheters reduce the pain and discomfort of delivering the occluding device to the intracorporeal location within the patient. Moreover, the small diameter catheter greatly increase the locations which these occluding devices can be deployed.

The spider segments of the occluding devices embodying features of the invention, which are suitable for implantation within a female patient's fallopian tubes, have expanded transverse dimensions of about 1 to about 5 mm, preferably about 2 to about 4 mm. The length of the occluding device for such uses may range from about 0.2 to about 3 inch (0.5-7.6 cm), preferably about 0.7 to about 1.5 inch (1.8-3.8 cm). Spacing between spider segments is usually selected to ensure that expansion and contraction of the spider segments do not interfere with the expansion and contraction of adjacent segments. Typically, an intrasegment spacing of about 0.1 to about 1 mm, preferably about 0.2 to about 0.8 mm as measured in the collapsed configuration. Additionally, the spider segment spacing of the device should not interfere with advancement and delivery of the device. Uses in other treatments and other intracorporeal locations may require different size occluding devices. About 1 to about 12, preferably about 3 to about 6 spider segments may be disposed along the length of the occluding device.

The occluding device embodying features of the invention may be provided with a material to facilitate tissue growth within the occluding device to effect lumen occlusion. Suitable materials include fibrous synthetic materials such as Dacron or Nylon and other materials such as collagen, tissue matrix or other material which encourages or supports tissue ingrowth. The fibrous materials may be deployed about or between the expansive members of the spider segments or the connectors between the spider segments. The various components of the occluding devices may be provided with porous jackets or surfaces for the same purpose.

The invention has numerous advantages over the art. The configuration of this invention provides for an occluding device that may be compressed into a very small diameter and delivered through a delivery catheter of very low profile. This allows for delivery systems with improved ease of use and the ability to use this device in combination with other devices where that would not be possible with an occlusion device of larger diameter. It provides for an expandable device that, once expanded and placed, may be very stationary and stable. If used in combination with other devices and attached to other deices, the occluding device may provide an excellent stable and stationary reference point or anchor when place in the tissue. The advantageous stationary reference point or anchor when placed in the tissue. The advantageous configuration provides an excellent drug delivery platform. Because of the configuration, the device is inexpensive and easy to manufacture. The use of a combination of subcomponents makes the over-all occlusive device highly versatile and adjustable to a great variety of advantageous configurations with the subcomponents widely spaced, or close together, or numerous, or few in number, depending on the desired use. It is highly efficient in its configuration, and otherwise very adaptable in ways that will be clear to one of skill in the art in view of the drawings and detailed description contained herein.

The delivery catheter may be of an over the wire (OTW) or of rapid exchange (RX) type design. An OTW catheter has a guide wire lumen extending the full length of the catheter, whereas an RX type catheter has a relatively short guide wire lumen in a distal portion of the catheter. With a rapid exchange type catheter, the guide wire lumen (as measured from a distal guide wire port to a proximal guide wire port) is about 0.5 to about 50 cm, typically about 10 to about 35 cm.

The alternative means of using a pushing device proximal to the collapsed device allows for the device to have a very small collapsed profile since no guide wire needs to pass through it, however such systems do not allow for any steerability of the system through the body lumens. For these reasons and others it would be desirable to have a small diameter system that still allows for steerability of the guide wire while advancing through the body passageways.

The present invention also provides devices that may be implanted into a body lumens (e.g., fallopian tube, vas deferens, bronchus, blood vessel or other anatomical passageway or lumen) of a human or veterinary subject to occlude that body lumen and/or to deliver a substance (e.g., a drug, a protein, cells, a biological material, a chemical substance, a gene therapy preparations, etc.) for at least a period of time following implantation of the device.

In accordance with the invention there is provided an implantable occlusion and/or substance delivery device of the foregoing character that comprises; a) an expandable intraluminal member which is i) disposable in a first configuration wherein it is sufficiently compact to be advanced into the body lumen and ii) subsequently expandable to a second configuration wherein the intraluminal member becomes implanted within the body lumen; and., b) a quantity of a substance disposed on or in the device such that the substance will be delivered from the intraluminal member into some target tissue for at least some period of time following implantation of the intraluminal member within the body lumen. In some embodiments, the intraluminal member may include a mesh material or other matrix designed to facilitate cellular or tissue ingrowth such that cells or tissue that ingrow into the device will effect occlusion of the body lumen in which the device is implanted. The present invention additionally includes systems wherein the implantable occlusion and/or substance delivery device is used in combination with a delivery catheter and/or guidewire and/or endoscopic device.

Further in accordance with the invention, there are provided methods for sterilization or contraception wherein a lumen occluding and/or substance delivering device of the foregoing character is implanted in a fallopian tube of a female subject or the vas deferens of a male subject. In such applications, the substance disposed on or in the device may comprise a contraceptive or spermicidal agent that will be delivered by the device in a concentration and form that is effective to cause a contraceptive effect in the subject, at least during a period of required for the implanted device to effect complete occlusion of the fallopian tube or vas deferens. Still further in accordance with the invention, there are provided methods for treating disorders or injuries of the lung by implantation of a lumen occluding and/or substance delivering device of the foregoing character within a bronchus, bronchiole or other anatomical passageway within the lung. In such applications, the device may occlude a bronchus to stop the flow of inspired air to a portion of the lung (e.g., a lobe or portion of a lobe) that is diseased or injured. In such applications, the substance disposed on or in the device may comprise an agent that causes a therapeutic effect in the lung such as an antimicrobial agent, mucolytic agent, bronchodilator, antiinflamatory, expectorant, antineoplastic agent, chemotherapeutic agent, immunomodulator, etc.

Still further in accordance with the invention, there are provided varied and universal methods for treating disorders or injuries of human or animal subjects by implanting a device of the foregoing character in a body lumen (e.g., a man-made lumen or a natural passageway within the body such as a blood vessel, lymphatic duct, duct of the biliary tree, etc.) so as to cause occlusion of that body lumen and to release a therapeutically or diagnostically effective amount of a substance for at least some period of time following implantation of the device.

Further aspects, elements and embodiments of the invention will become apparent to those of skill in the art upon reading and consideration of the detailed description set forth herebelow and the accompanying drawings to which it refers.

BRIEF DESCRIPTION OF THE DRAWINGS

FIGS. 11, 11A and 11B are elevational views of an occluding device having a single spider segment with various non-traumatic ends.

FIG. 11F is an elevational view of an occluding device having a single spider segment.

FIG. 11G is a close-up cross-sectional view of a non-traumatic end of FIG. 11F.

FIGS. 11H-11I are close up top-views of alternate non-traumatic ends of FIG. 11F.

FIG. 14A is an elevational view, partially in sectional view, of a rapid exchange-type delivery catheter illustrating the advancement of an occluding device embodying features of the invention.

FIGS. 14B and 14C are transverse cross-sectional views of the delivery catheter and guide wire shown in FIG. 14A taken along the lines 6-6 and 7-7 respectively.

FIG. 14D is an elevational view of an over-the-wire type delivery catheter.

FIG. 14E is a transverse cross-section of the over-the-wire delivery catheter shown in FIG. 14D, taken along the lines 9-9.

FIG. 14F is an elevational view, partially in section, of the distal section of the over-the-wire delivery catheter shown in FIG. 14D illustrating the advancement of an occluding device embodying features of the invention within the inner lumen of the delivery catheter by a pusher element after the guidewire has been withdrawn.

FIG. 14G is an elevational view, partially in section, of an over-the-wire delivery catheter with a combined guide wire-pusher element advancing an occluding member embodying features of the invention through the inner lumen of the catheter.

FIG. 14H is a transverse cross-sectional view of the delivery catheter shown in FIG. 14I taken along the lines 12-12.

FIG. 16A is an elevational view of an occluding device contained with a delivery catheter.

FIG. 16B is an elevational view of the released occluding device shown in FIG. 16A.

FIG. 18A is an exploded perspective view of one embodiment of system of the present invention comprising a lumen occluding/substance delivery device as shown in FIGS. 17A and 17B, in combination with a delivery cannula and a pusher device.

FIG. 18B is a perspective view of the system of FIG. 18A wherein the pusher has been used to expel the lumen occluding/substance delivery device out of the distal end of the delivery catheter.

FIG. 19A is a partial longitudinal sectional view of another embodiment of system of the present invention designed for over-the-wire delivery of the implantable device.

FIG. 19B is a showing of the system of FIG. 19A with the guidewire protruding from the distal end of the delivery catheter.

FIG. 21 is an enlarged perspective view of a lumen occluding/substance delivery device of the present invention having an optional substance delivery and/or ingrowth supporting matrix thereon.

FIG. 21A is an enlarged, cut away view of a portion of the substance delivery and/or ingrowth supporting matrix of the device of FIG. 21 illustrating one way in which the substance delivery and/or ingrowth supporting matrix may be constructed to deliver a substance following its implantation within the body of a patient.

FIG. 21B is an enlarged view of a portion of the substance delivery and/or ingrowth supporting matrix of the device of FIG. 21 illustrating another way in which the substance delivery and/or ingrowth supporting matrix may be constructed to deliver a substance following its implantation within the body of a patient.

DETAILED DESCRIPTION THE INVENTION

Figure 1:
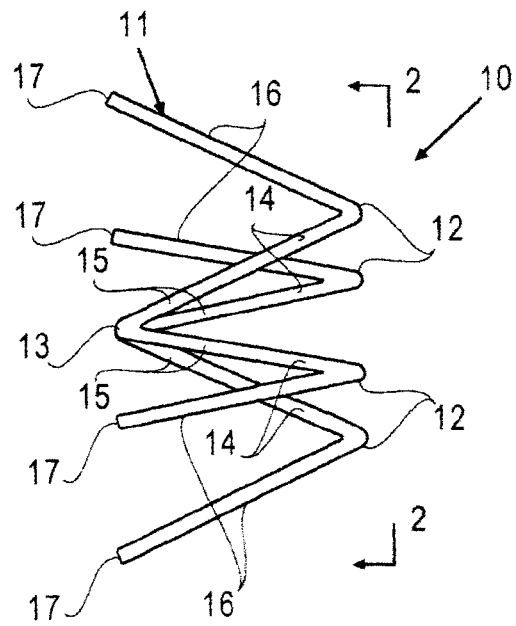
FIG. 1 is an elevational view of a prior art occluding device.

FIG. 1 illustrates a prior art occluding device 10 which is suitable to occlude a patient's reproductive lumen. The occluding device 10 is in the form of a spider segment 11 that has a plurality of expansive elements 12 which radiate from a central location 13. The expansive elements have first sections 14 with a first end 15 secured to the central location 13 and second sections 16 with free ends 17 radially displaced from the central location 13 in the expanded configuration as shown.

Figure 2:
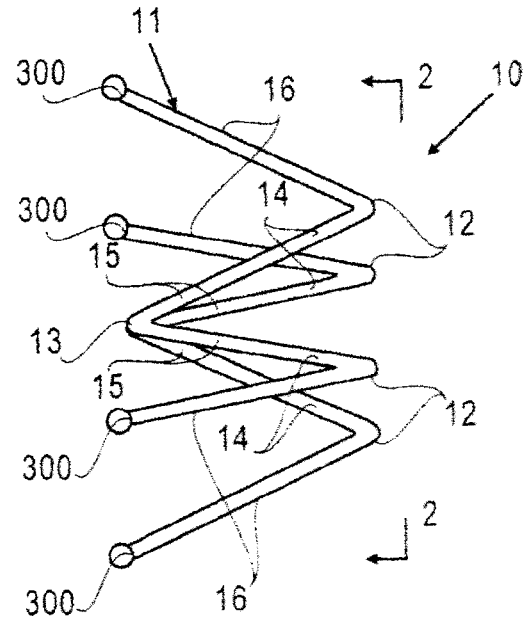
FIG. 2 is an elevational view of an occluding device having a single spider segment.
Figure 3:
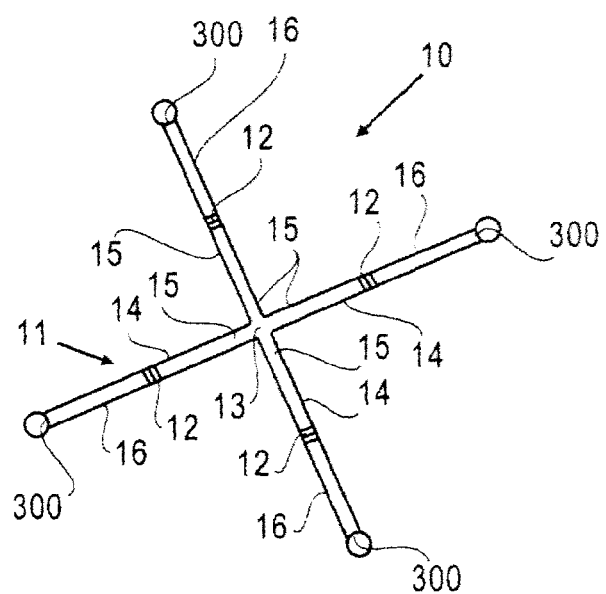
FIG. 3 is an end view of the occluding device shown in FIG. 1.

FIGS. 2 and 3 illustrate a occluding device 10 which is suitable to occlude a patient's reproductive lumen. The occluding device 10 is in the form of a spider segment 11 that has a plurality of expansive elements 12 which radiate from a central location 13. The expansive elements have first sections 14 with a first end 15 secured to the central location 13 and second sections 16 with non-traumatic ends 300 radially displaced from the central location 13 in the expanded configuration as shown. The central location 13 need not be the geometric center of the device 10. For example, it may be off set from the geometric center and be provided with expansive elements of different lengths.

Figure 4:
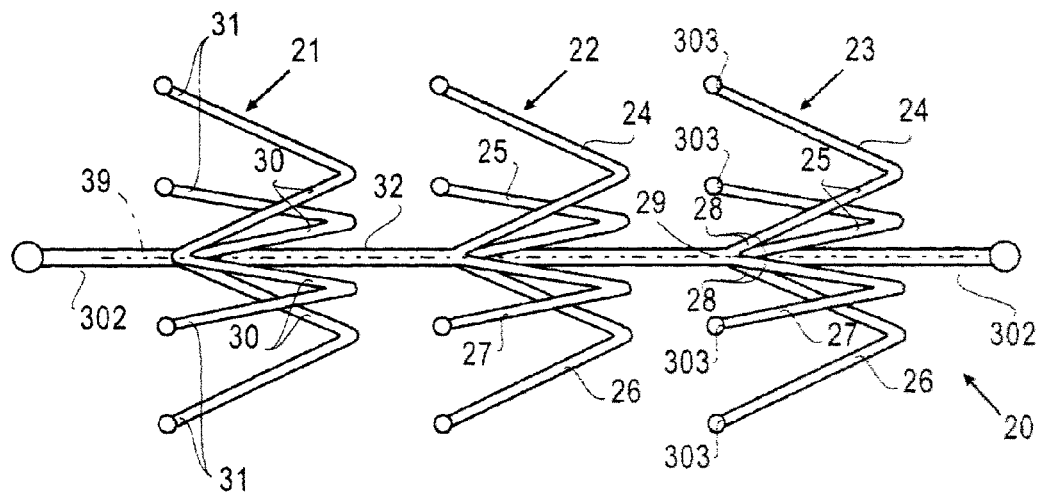
FIG. 4 is an elevational view of an occluding device having a plurality of interconnected spider segments in expanded configurations.

FIG. 4 represents an elevational view of an occlusion device 20 with three spider segments 21, 22 and 23 that have the same structure as the spider segment 11 shown in FIGS. 1 and 2. The individual spider segments 21-23 have expansive elements 24, 25, 26 and 27 which are secured by a first ends 28 to the central location 29. Each expansive element of a spider segment has a first section 30 which is adjacent to the central location or center line axis 39 and which is oriented toward one end of the occluding member 20 and a second section 31 which is oriented toward the other end of the occluding device 20. The angle between the first and second sections 30 and 31 of the expansive elements ranges from about 20 degrees to about 75 degrees, preferably about 30 degrees to about 60 degrees. The spider segments 21 and 22 are interconnected by beam 32 and spider segments 22 and 23 are interconnected by beam 33 both of which lie along the center line axis 29. The beams 32, 33, may be straight or curved. Extension members 302 extend past the ends of the spider segments and have ball ends. The non-traumatic ends 303 of the expansive elements 24-27 are configured to engage the interior body lumen, without completely piercing the lumen wall, and seat the occlusion device therein.

Figure 4A:
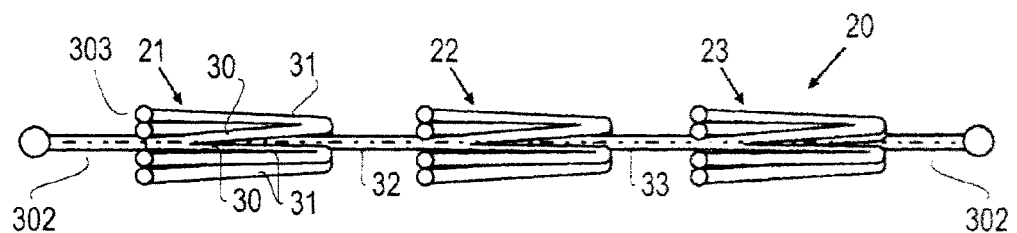
FIG. 4A is an elevational view of the occluding device shown in FIG. 4 compressed into a contracted configuration, which is typically the configuration that is used when delivering the device to a location such as a fallopian tube.

FIG. 4 illustrates the occlusion device 20 in an expanded configuration and FIG. 4A illustrates the device 20 compressed into a constricted configuration with the first and second sections 30 and 31 of the expansive elements 24-27 folded together so as to present a smaller profile.

Figures 5A, 5B, 5C, 5D:
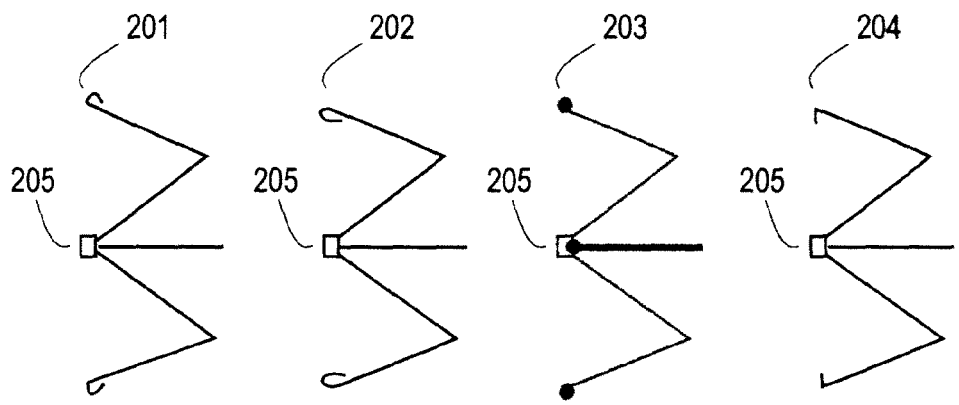
FIGS. 5A-5D are elevational views of various occluding devices illustrating various non-traumatic ends.

FIGS. 5A-5D illustrate occlusion devices as previously described with various non-traumatic ends. In FIG. 5A non-traumatic end 201 is formed from a contoured wire bent over itself away from the central location 205. In FIG. 5B non-traumatic end 202 is formed from a contoured wire bent over itself towards the central location 205. In FIG. 5C the non-traumatic end 203 is a ball shape element. In FIG. 5D non-traumatic end 204 is a contoured wire bent with a tight radius angled towards the central location 205. An occluding device may also include a combination of different non-traumatic ends. The central location 205 may be made out of a ring to crimp, solder, or use to attach to the members 206.

Figure 6:
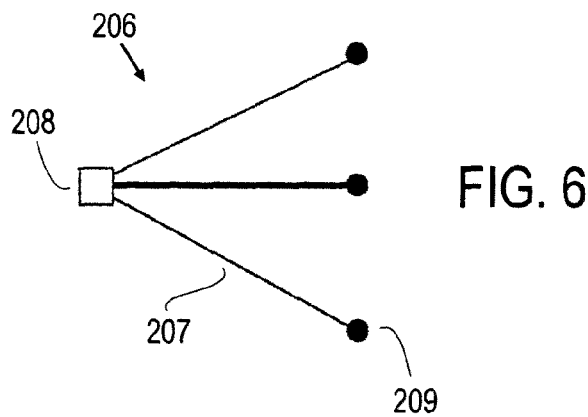
FIG. 6 is an elevational view of the occluding device having a single spider segment.

FIG. 6 illustrates an example of an occlusion device. The occluding device 206 is in the form of a spider that has a plurality of expansive elements 207 which radiate from a central location 208. The expansive elements are secured to the central location 208 with non-traumatic ends 209 radially displaced from the central location 208 in the expanded configuration as shown. The non-traumatic ends are shown as a ball shape element, but may also include any of the other examples in this specification.

Figure 7:
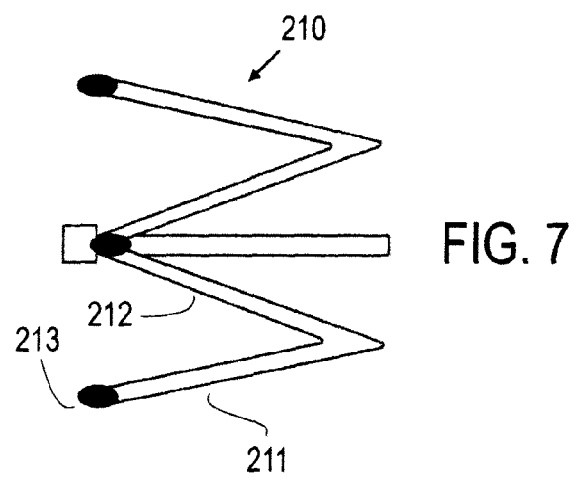
FIG. 7 is an elevational view of the occluding device having a single spider segment.

FIG. 7 illustrates an example of an occlusion device. The occluding device 210 shares the basic construction as the occluding device shown in FIG. 2. In this example the members 211, 212, are formed from flat-shaped wire. An occlusion device may also have a combination of flat and round members. The central location and the non-traumatic ends are on the same side of the device. The non-traumatic ends 213 are shown as a ball shape, but may also include any of the other examples in this specification.

Figure 8A:
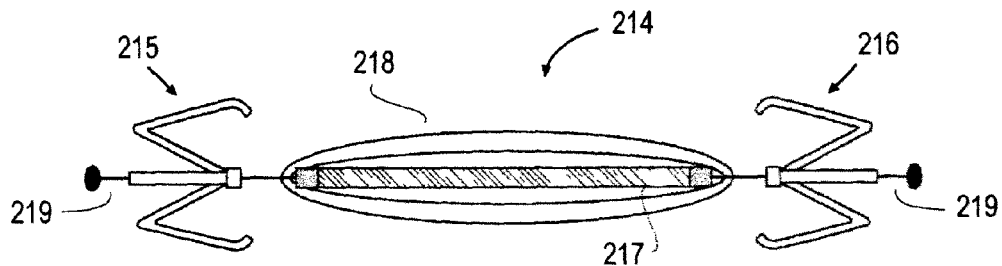
FIGS. 8A-8D are elevational views of occluding devices having a plurality of interconnected spider segments in expanded configurations.

FIGS. 8A-8D illustrate examples of occlusion devices. In FIG. 8A opposing spider segments 215, 216, are located at both ends of the device 214. An inner coil 217 makes up the center section of the device. Fiber strands 218 (e.g. dacron fibers or other fibers designed to elicit and promote tissue in-growth) are interdisposed between the opposing spider segments to promote tissue growth. Extension members 219 extend past the opposing spider segments which include non-traumatic elements.

Figure 8B:
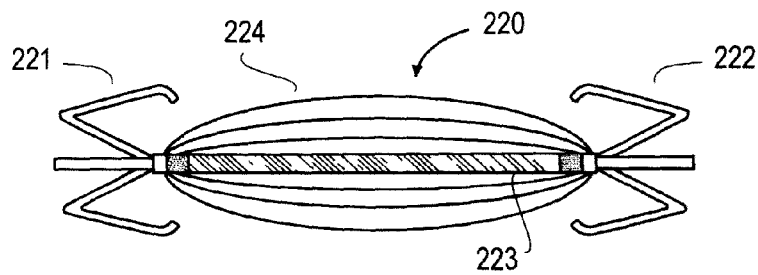

FIG. 8B illustrates an example of an occlusion device 220. Opposing spider segments 221, 222, are located at both ends of the device. An inner coil 223 makes up the center section of the device. The inner coil may be hollow to allow installment by means of a guidewire. Fiber strands 224 are interdisposed between the opposing spider segments to promote tissue growth.

Figure 8C:
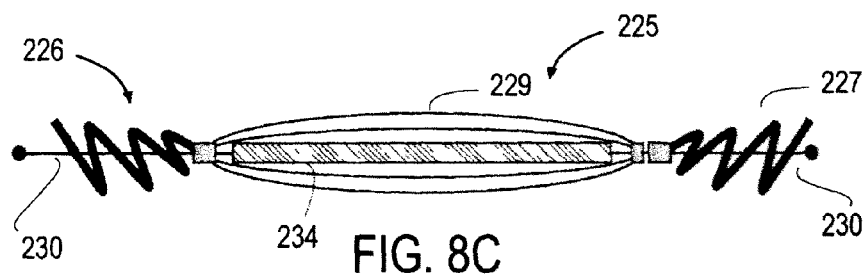

FIG. 8C illustrates an example of an occlusion device 225. Opposing coil segments 226, 227, are located at both ends of the device. An inner coil 228 makes up the center section of the device. Fiber strands 229 are interdisposed between the opposing spider segments to promote tissue growth. Extension members 230 extend past the opposing spider segments.

Figure 8D:
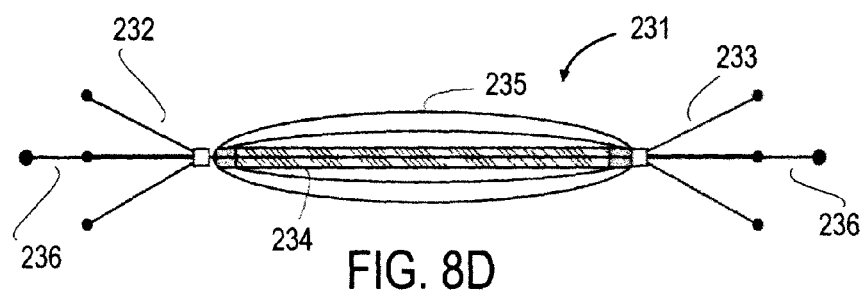

FIG. 8D illustrates an example of an occlusion device 231. Opposing spider segments 232, 233, are located at both ends of the device. In this example the spider segments share construction of the example in FIG. 6. An inner coil 234 makes up the center section of the device. Fiber strands 235 are interdisposed between the opposing spider segments to promote tissue growth. Extension members 236 extend past the opposing spider segments.

Figure 9A:
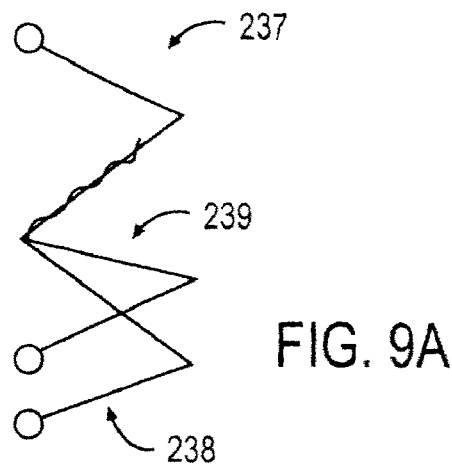
FIGS. 9A-9B are elevational views of occluding devices having a single spider segment.
Figure 9B:
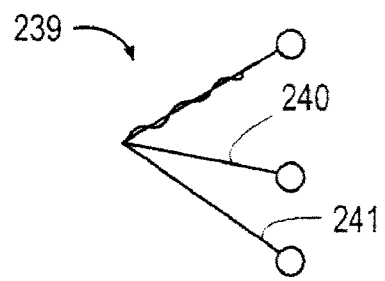

FIGS. 9A and 9B illustrate examples of occlusion devices. In FIG. 9A the device 237 shares the basic construction of the example in FIG. 2. The device is constructed from two wires 238, 239. The first wire 238 is formed in a rough "M" shape. The second wire 239 is formed into a rough "N" shape. One leg of the second wire 239 is coiled around one of the inner members of the first wire 238. The device 239 in FIG. 9B shares the basic construction of the example in FIG. 6. The device is constructed from two wires 240, 241. Both wires 240, 241 are formed in a rough "V" shape. One leg of the first wire 240 is coiled around a leg of the second wire 241. This construction method does not require soldering, welding, or bonding, although it does not preclude additional fastening techniques. The wires may be coiled first and then formed into desired shapes.

Figure 10A:
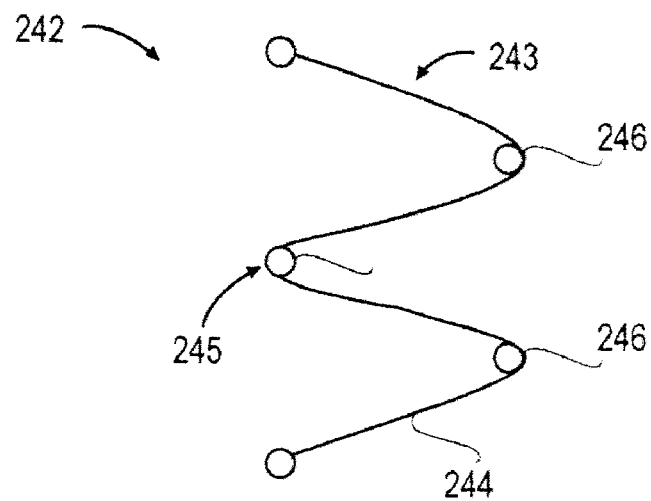
FIGS. 10A-10B are elevational views of occluding devices having a single spider segment.
Figure 10B:
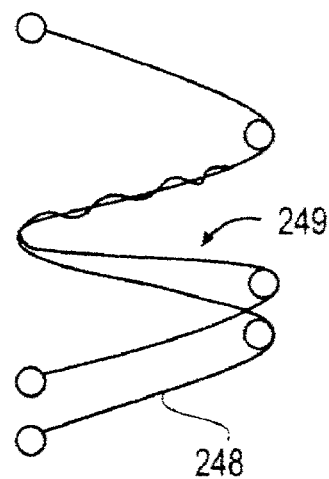

FIGS. 10A and 10B illustrate examples of other occlusion devices. The device 242 in FIG. 10A has two expansive elements 243, 244, and a central location 245. The device is formed from one wire and utilizes coils 246 to add spring force when expanded. More expansive force may be necessary to counter act peristaltic and ciliated forces. A fewer amount of coils may be used to add less force. The device in FIG. 10B is formed from two basic elements 248, 249, both being largely what is shown in FIG. 10A. The construction method illustrated in FIGS. 9A and 9B is used to unite the elements to form a total of three expansive elements. In other words, and end of element 248 is coiled around a portion of element 249.

FIGS. 11-11I illustrate examples of occlusion devices with various non-traumatic ends. All devices share the basic construction of the example in FIG. 2.

In FIG. 11 device 250 has non-traumatic ends 251, 252. Non-traumatic ends 251,252 are examples of ends which hold into but still prevent the members 257 from piercing a body lumen, which may be necessary to counter act peristaltic and ciliated forces. As shown in FIG. 11A non-traumatic end 251 illustrates a flattened or ribbon section with a spike 253. FIG. 11B shows a non-traumatic end 252 with a spike 255 on a ball 256. The height of the spikes 253, 255 may be chosen so as to not completely pierce a body lumen. The ledge 254 and the ball 256 also provide stops to prevent the members from completely piercing a body lumen.

Figure 11C:
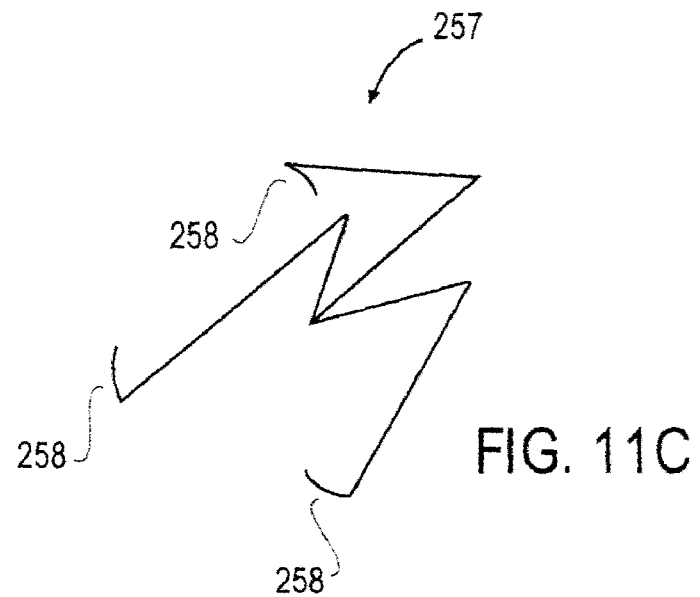
FIGS. 11C-11D are an isometric and end view respectively of an occluding device having a single spider segment.
Figure 11D:
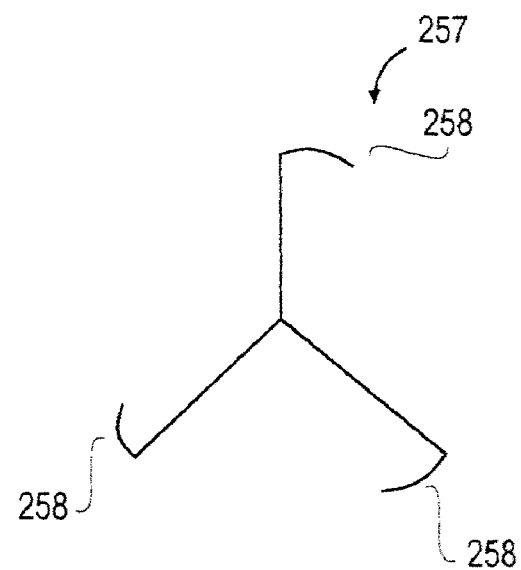
Figure 11E:
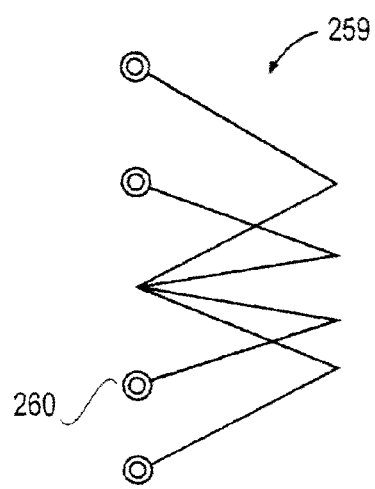
FIG. 11E is an elevational view of an occluding device having a single spider segment.

FIGS. 11C and 11D illustrate an example of an occlusion device 257. FIG. 11C is an isometric view and FIG. 11D is a frontal view. The non-traumatic ends 258 are formed such that they engage a body lumen with a large amount of dragging surface area, which may be necessary to counter act peristaltic and ciliated forces. In this example the non-traumatic ends 258 are formed as arcs. When placed inside a body lumen, the arcs are generally concentric with the lumen. FIG. 11E illustrates an example of an occlusion device 259. In this example the non-traumatic ends 258 are formed as spirals. When placed inside a body lumen, the spirals are generally parallel with the walls of the lumen.

FIGS. 11F-11I illustrate examples of an occlusion device 261. In this example the non-traumatic ends 262 are formed as pads. When placed inside a body lumen, the pads are generally parallel with the walls of the lumen. The pads may be molded and subsequently bonded onto the device. FIG. 11G shows a close-up cut-away view of a pad 262. FIG. 11H shows a close top view of a pad 262, in this example the pad is textured to provide friction against peristaltic and ciliated forces. FIG. 11I shows an alternate example of a pad 263. Pad 263 has a porous structure. Drugs (not shown) or fibers 264 may be placed inside or attached to the pores to provide therapy, and promote tissue in-growth into the fallopian tube. The other types of non-traumatic ends shown and/or described herein may also be modified to include pores or depots which include drug eluting substances and/or dacron (or other types of) fibers which are designed to elicit tissue in-growth in order to occlude a body lumen such as a fallopian tube (and thereby act as a contraceptive device). The dacron (or other types of) fibers may alternatively be applied (e.g. by gluing with a biocompatible glue) to the non-traumatic ends without pores or depots.

Figure 12A:
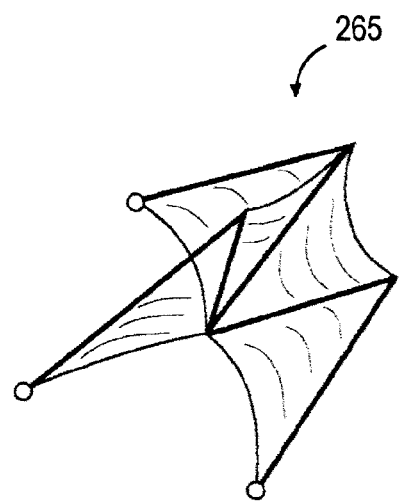
FIGS. 12A-12B are isometric and elevational views of an occluding device having a single spider segment with a membrane.
Figure 12B:
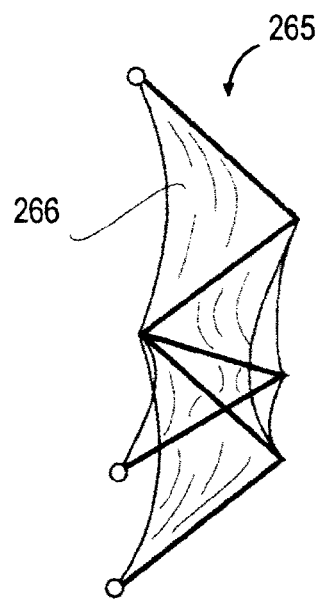

FIGS. 12A and 12B illustrate an example of an occluding device 265. FIG. 11A is an isometric view of the device 265. FIG. 12B is a side view of the device 265. This device shares the basic construction of the example in FIG. 2. A membrane 266 is inter-disposed between the members. The membrane may be dissolvable and have a contraceptive in it or other drug inside it. Once placed in a body lumen, the membrane can dissolve relatively instantly or over an extended period of time to deliver the desired therapy. The membrane may also be made from a material, such as expanded PTFE, which helps promote tissue growth.

Figure 13A:
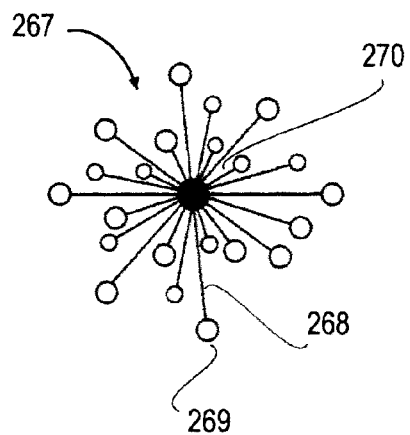
FIG. 13A is an elevational view of an occluding device having a single brush element.
Figure 13B:
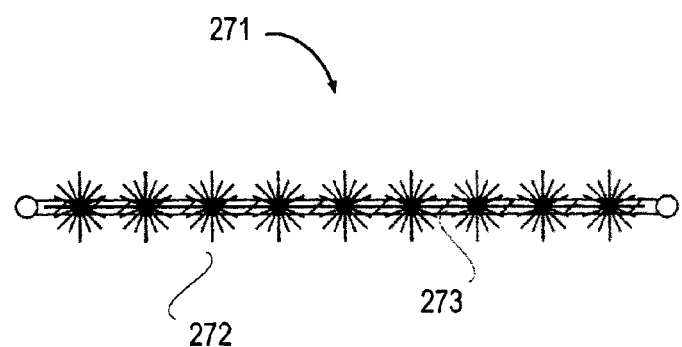
FIG. 13B is an elevational view of an occluding device having a plurality of brush elements.

FIGS. 13A and 13B illustrate an example of an occluding device. In FIG. 13A the occluding device 267 consists of a brush element which has a plurality of members 268 with non-traumatic ends 269 radiating from a central location 270. The members may be interwoven or knotted at the central location. In the example shown the non-traumatic ends form a generally spherical shape with a circular cross section. The occluding device 271 in FIG. 13B consists of a plurality of brush elements 272. The brush elements are connected with an elongated connecting member 273. The ends of the brush elements may include non-traumatic ends. The elongated connecting member may be constructed out of a plurality of coiled wires. In the example shown there is spacing between the brush elements 272, however the brush elements may be close enough in spacing to form a cylindrical contour. The examples in FIGS. 13A and 13B may further include fibers which are designed to elicit and promote tissue in-growth.

FIGS. 14A-14C show a rapid exchange delivery catheter 40 suitable to deliver an occluding member 10 as shown in FIG. 2. The delivery catheter 40 has an elongated shaft 41 with a proximal shaft section 42 and a distal shaft section 43. The elongated shaft 41 has a lumen 44 which extends the length of the shaft to the discharge port 45 in the distal end 46 in the distal shaft section 43. The distal shaft section 43 has a second lumen 47 for receiving a guide wire 48 over which the delivery catheter is advanced to the desired intracorporeal location for deploying the occluding device. A pusher element 50 having an elongated shaft 51 has an enlarged head 52 on the distal end thereof to engage an occlusion member 10 slidably disposed within the inner lumen 44. The pusher element 50 is long enough so that the proximal end 54 of the shaft 51 extends out of the proximal end 55 of the catheter 40 when the enlarged head 52 thereof has pushed the occlusion member 10 out the discharge port 45 in the distal end 46 of the catheter into a body lumen. The guide wire 47 is slidably disposed within the short guide wire lumen 47 which may be about 0.5 to about 50 cm, preferably about 10 to about 35 cm in length. A distal guide wire port 56 is provided in the distal end 46 of the catheter 40 and a proximal guide wire port 57 is provided a short distance proximal from the distal guide wire port and a substantial distance from the proximal end 55 of the catheter. The guide wire 47 may be of conventional structure with an elongated shaft 58, a tapered distal shaft section 59 and a shapeable spring tip 60 which enables steering the distal end of the guide wire within the patient's body lumen by torquing the proximal end 61 which is configured to extend out of the patient's body.

When delivering the occlusion device 10 by means of a rapid delivery catheter 40, the guide wire 47 is usually advanced through the patient's vaginal canal and uterine cavity and into the patient's fallopian tube with a hysteroscope. The shaped spring tip 60 on the distal end of the guide wire 47 may be used to guide the distal tip into the patient's fallopian tube. The guide wire 47 is advanced until the spring tip 60 is disposed distal to the desired location for the occluding member 10. The rapid exchange delivery catheter 40 may then be advanced over the guide wire until the distal end of the delivery catheter 40 is in an appropriate position for the delivery of the occluding device within the patient's body lumen. The pusher element 50 is then distally advanced until the enlarged head 52 pushes the occluding device 20 out the discharge port 45 in the distal end 46 of the delivery catheter 40. The occlusion device 10 expands upon deployment from the delivery catheter 40 and then the delivery catheter and guide wire 47 may be removed from the patient.

The movement of the pusher rod and occluding device within the catheter, of course is relative. That is, in one application, the enlarged head may be held stationary in the longitudinal direction, and the catheter with the occluding device therein may be withdrawn, causing the enlarged head to contact and expel the occluding device from within the catheter. Relative to the body lumen, such as the fallopian tube, however, the occluding device does not move. The catheter that is withdrawn and the occlusive device is laid down in the fallopian tube as the catheter is withdrawn. This has the advantage of allowing the occlusive device to be expelled from the catheter lumen into the fallopian tubes so that the occlusive device does not move in a longitudinal direction within the fallopian tube. Since the occlusive device may consist of several spider segments, and since the first one expelled from within the catheter will often expand and engage the wall of the fallopian tube immediately upon release from the confines of the lumen 44, it may be important not to attempt to push the occlusive device in a longitudinal direction once it has begun to attach to the fallopian tube walls.

FIG. 14D-14F depict an over-the-wire type delivery catheter 70 which has an elongated shaft 71, an inner lumen 72, a distal port 73 in the distal end 74 of the shaft and an adapter 75 on the proximal end 76 of the shaft. As shown best in FIG. 14F a pusher rod 77 with enlarged head 78 is slidably disposed within the inner lumen 72. The enlarged head 78 is configured to engage the proximal end of occlusion device 20 which is disposed within the inner lumen 72 in a constricted configuration. Distal movement of the pusher rod 77 advances the occlusion device 20 through the inner lumen and out the distal port 73 in the distal end 74.

An alternative delivery system is shown in FIGS. 14G-14H wherein a pusher rod 80 is slidably disposed within an inner lumen 81 of delivery catheter 82. The pusher rod 80 has an elongated shaft 83, an enlarged head 84 and a distal shaft section 85 extending from the front face 86 of the enlarged head 84 is provided with a distal spring tip 86. The pusher rod 80 is in effect a combined pusher rod-guide wire which both guides the delivery system to the desired location and pushes an occlusion device 10 out of the discharge port 87 in the distal end 88 of the delivery catheter 82.

Figure 15A:
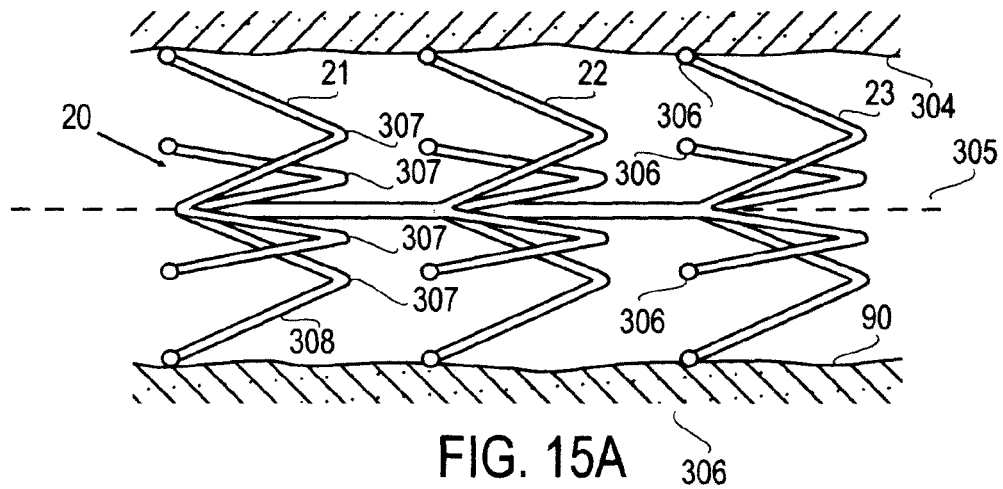
FIG. 15A is an elevational view of an occlusion device embodying features of the invention disposed within a body lumen such as a female's fallopian tube.

FIG. 15A illustrates an occlusion device 20 embodying features of the invention disposed within a patient's body lumen such as a female patient's fallopian tube 90. The spider segments 21, 22 and 23 of the occluding device 20 has expansive elements with non-traumatic ends 306 which engage the inner lining of the body lumen without completely piercing the lumen. Four expansive elements per member are shown, but more or less may be used. The reproductive lumen has a longitudinal axis 305. The non-traumatic ends form an expansive diameter, relative to the longitudinal axis of the reproductive lumen, into the patient's reproductive lumen 304. The second ends 307 of the inner members 308 also form an expansive diameter. The spider segments 21, 22, and 23 are joined together to form one contiguous unit. Fibers which are designed to elicit and promote tissue in-growth into the fallopian tube may also be added to the occlusion device as shown in FIG. 15A.

Figure 15B:
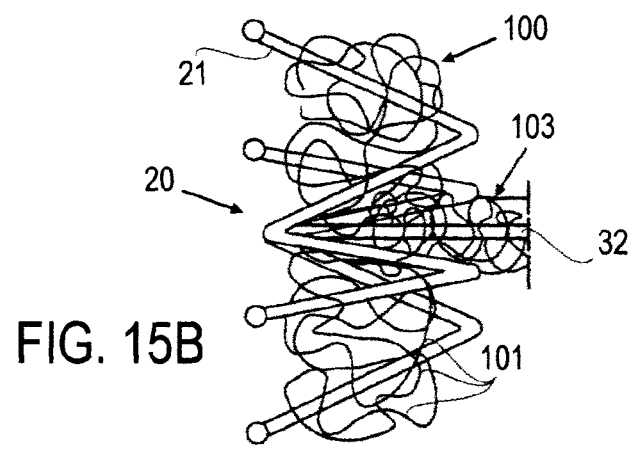
FIG. 15B is a partial elevational view of the occluding device shown in FIG. 14A with fibrous material disposed about the expansive elements and a connecting member.

FIG. 15B illustrates the proximal portion of occlusion device 20 shown in FIG. 3 depicting the expansive elements of spider segment 21 provided with fibrous mass 100 of strands 101 which facilitate tissue ingrowth when the occlusion device is deployed in a female patient's fallopian tube. A similar fibrous mass 103 may be positioned about the connecting beam 32 which extends between the spider segments 21 and the adjacent spider segment 22 (not shown). While fibrous masses of strands are depicted in FIG. 14, a variety of materials which facilitate tissue growth within the occluding device to facilitate luminal occlusion may be used to facilitate sufficient tissue ingrowth to effectively occlude the body lumen. The fibrous material is preferably a polyester such as polyethylene terephthalate (PET) Hytrel or a polyamide such as Nylon 6 or ePTFE. Other biocompatible polymeric materials may be employed which facilitate the in-growth of tissue into the device to facilitate effective occlusion of the body lumen. Open cell or closed cell foams or sponges of these or other materials may be used.

Figure 15C:
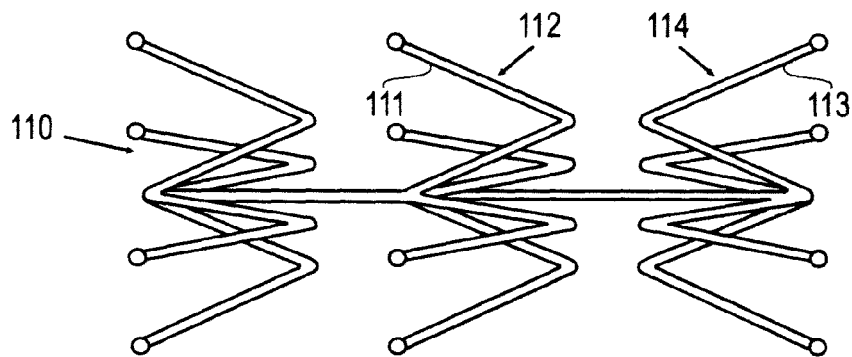
FIG. 15C is an elevational view of an occluding device having a plurality of interconnected and opposing spider segments in expanded configurations.

FIG. 15C illustrates an alternative design for an occlusion device 110 in which the expansive elements 111 of one spider segment 112 are oriented in an opposed orientation to the expansive elements 113 of an adjacent spider segment 114. With the non-traumatic ends of multiple spider segments in opposing directions, the occluding device 110 is more securely disposed within the patient's body lumen so as to minimize displacement.

FIG. 16A illustrates an occlusion device 273 in an unexpanded form inside of a delivery catheter 274. The extension member 275 is extended.

FIG. 16B illustrates the occlusion device 273 in an expanded configuration. The spiders share the construction generally shown in FIG. 6. In this example the expansive elements 276 are formed in to an "S" bend to add expansion force, however straight expansive elements may also be used. Various non-traumatic ends are also illustrated, however identical or different non-traumatic ends may be used in conjunction with each other.

Figure 16C:
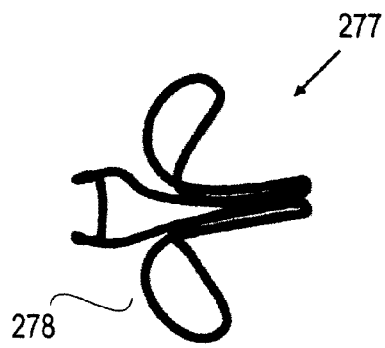
FIG. 16C is an elevational view of an expanded occluding device with flower petals elements.

FIG. 16C illustrates an occlusion device 277 in an expanded form. The occlusion device 277 features non-traumatic elements 278, which resemble flower petals and may be referred to as flower petal ends. The flower petal ends 278 are formed from looped continuous members. Due to the shape of the elements, they will have a non-traumatic ends interfaced with the fallopian tube, but have enough surface area and expansive force to maintain their position inside the fallopian tube. In the example shown, three flower petal elements are used, however more or less may be used.

Figure 16D:
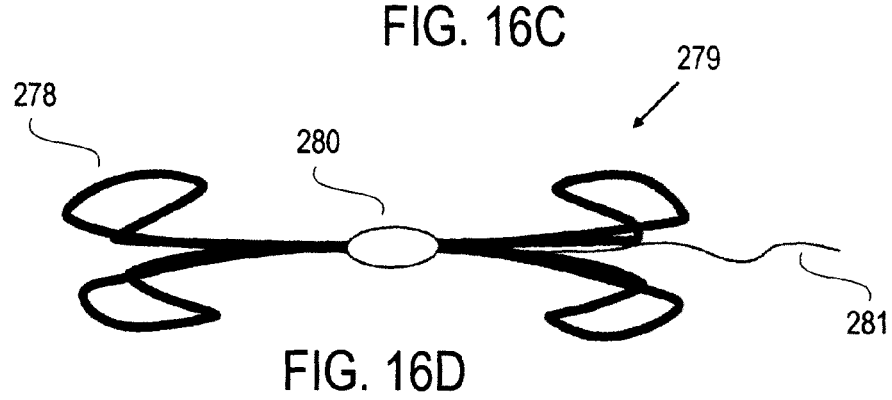
FIG. 16D is a side view of an expanded occluding device with flower petals elements and unexpanded hydrogel center.

FIG. 16D illustrates an occlusion device 279 in an expanded form. In the shown example only two flower petal elements 278 are used on each side of the device 279, however more than two flower petals elements may also be used. Flower petal elements 278 may also be used on devices as shown in FIG. 16B. The occlusion device 279 also features an unexpanded hydrogel center 280. The hydrogel center 280 may serve to connect the flower petal ends to one another. Multiple or single hydrogel centers 280 may also be used in various positions on a longer device, such as shown in FIG. 16B, such as the center or ends. The occlusion device also features an optional marker string 281 which is designed to be seen on the proximal end of the device 279 and to extend out into the uterus after proper placement of the device 279 within the fallopian tube. The marker string 281 serves to show proper placement of the occlusion device 279 inside the fallopian tube, as visible from a hysteroscope inside the uterus. The marker string 281 may be polymer or a bio-absorbable suture type material.

Figure 16E:
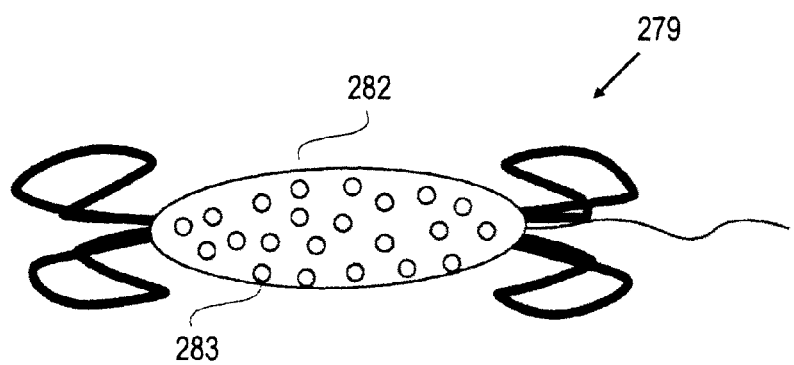
FIG. 16E is a side view of an expanded occluding device with flower petals elements and expanded hydrogel center.
Figure 17A:
FIG. 17A is a side view of one embodiment of a lumen occluding and/or substance delivery device according to the present invention, disposed in a collapsed configuration (as it may exist when being delivered in a delivery device).
Figure 17B:
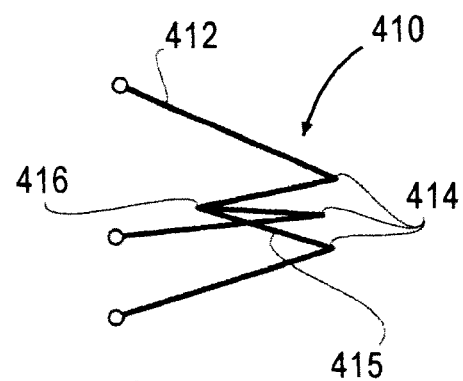
FIG. 17B is a side view of the device of FIG. 17A, disposed in an expanded configuration.
Figure 17C:
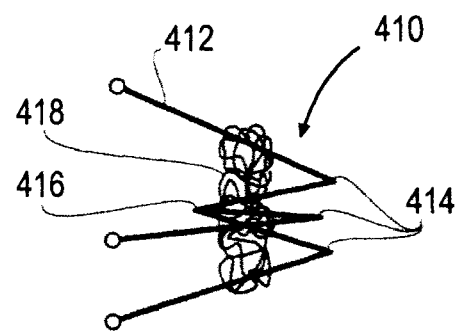
FIG. 17C is a side view of the device of FIGS. 17A and 17B, disposed in an expanded configuration and having an optional substance delivery and/or ingrowth supporting matrix thereon.

FIG. 16E illustrates the occlusion device 279 after placement inside a fallopian tube. The expanded hydrogel center 282 will absorb liquids to completely block the fallopian tube soon after or immediately upon placement, and before tissue grows into the fallopian tube, thus providing an immediate contractive effect. The expanded hydrogel center 282 features an optional porous construction 283 to facilitate tissue in growth; alternatively the expanded hydrogel center may be solid. The expanded hyrdogel center may also contain time released drugs or hormones to facilitate tissue in growth and/or contraceptive protection. The device may be fabricated from materials which promote tissue growth, such as polymer (e.g. polyester, PET, etc.). For example, the entire structure of the device 279 may be fabricated out of such a polymer. The polymer may be molded with or without a small nitinol wire inserted into the center of the mold to give the device a proper amount of superelasticity. The polymer may be doped with a radiopaque material, such as beryllium sulfate. In another embodiment, the device 279 may be a metal device which is coated with a material which promotes tissue growth (without having any fibers, such as Dacron fibers).

Alternatively, drugs and/or hormones may be incorporated within the device in order to accelerate tissue growth into the device, or in or on any of the structural componenets of the occlusive device, or in or on the fibrous masses or strands. Alternatively, if occluding the fallopian tube of a female patient, the device may also elude contraceptive drugs or, if occluding a male patient's reproductive lumen, a spermicide to ensure that the occluding device will be effective immediately upon placement, rather than having to wait for sufficient tissue in-growth into the device for effective occlusion.

The delivery catheter may provide for the delivery of two or more occluding devices. If more than one occluding device is to be delivered within the body (e.g. an occluding device to each fallopian tube), there is no need to remove the initial delivery catheter to deliver additional devices. In such an instance, the physician may deliver one device to the first of two fallopian tubes, and, then access the other fallopian tube with the delivery catheter where the second occluding device is deployed. The use of two occluding devices has the advantage of speeding the overall procedure time and reducing overall costs for the procedure because only one delivery catheter is used.

In another embodiment a length of shaft along the distal end of the delivery catheter is colored a different color than the body of the catheter. As the delivery catheter is advanced through a hysteroscope, the change in color on the distal end of the delivery catheter can be viewed through the hysteroscope as the distal end of the catheter enters the fallopian tube. When the color changed portion disappears from view because it is completely located within the fallopian tube, the enclosed occlusion device is properly located at the specified depth. The occlusion device may then be delivered, ensuring that it is placed at a predetermined depth within the fallopian tube. Depending on the length of the visual marker on the distal end of the delivery catheter, the occlusion device may be located within the isthmic region of the fallopian tube, distal to the isthmic region, or even near the ampulla region of the fallopian tube. An alternative to the variable colored distal region is a visual marker on the delivery catheter. As the visual marker enters the fallopian tube, the occlusion device is at the proper depth for deployment. Alternatively, two markers may be placed to show a pre-specified range of depth indication proper placement. Visual markers on the distal end of the delivery catheter may include raised portions or bumps on the exterior of the distal tip of the delivery catheter.

Similarly visual markers such as colored segments, marker lines, or bumps may be located along the length of the guide wire shaft to aid the physician in proper placement of the guide wire. for example, the color bands or other markings may be used to indicate the depth of insertion of the end of the guide wire into the fallopian tubes so that it is properly placed before the Rx catheter is advanced along the guide wire. such markings on the guide wire shaft may also allow the physician to view the guide wire shaft through the hysteroscope and check any movement of the guide wire to prevent inadvertently pushing the guide wire too deep into the fallopian tube when advancing the catheter over the guide wire after the guide wire is initially placed into the fallopian tube.

An alternative to visual means of placement is the use of ultrasound guidance. In this case, a marker that is echogenic is placed on the distal tip of the delivery catheter and a second marker locating the occlusion device within the delivery catheter allows for proper placement of the device under ultrasonic guidance.

Another means of placement for the device is under fluoroscopic guidance. In this case, a radiopaque marker is located at the distal tip of the delivery catheter and a second marker locates the occlusion device within the delivery catheter. When the proper depth of the delivery catheter within the fallopian tube has been seen under fluoroscopy, the occlusion device is ready to be deployed. Additionally, the occlusion device itself may be made radiopaque, either in part or in whole, allowing for direct visualization under fluoroscopy and easier placement.

The devices, systems, and methods of this invention may be used in the occlusion of various body passageways. For example, the occluding devices of the invention may be used to occlude arteries leading to tumors and other undesirable tissue. Additionally, the devices are particularly well-suited for the steerable delivery of small self expanding intravascular devices, including coronary and neurovascular stents. The devices and methods described herein may be placed using visual means, ultrasonic guidance and/or fluoroscopy.

The occluding members embodying features of the invention may be preferably formed at least in part of superelastic NiTi alloy with an austenite to martensite transition temperature less than 40.degree. C. preferably less than 25.degree. C. The occlusion device formed at least in part of superelastic NiTi alloy may have the austenite transformed to martensite by reducing the temperature of the device to below the transformation temperature and then constricting the occluding device to facilitate entry into the inner lumen of the delivery catheter in the martensite phase. The mechanical constriction of the occluding device within the delivery catheter maintains the occluding device in the martensite phase. Alternatively, the device may be mechanically compressed to stress-induce the austenite to martensite transformation. When the NiTi devices are released from the delivery catheter, the NiTi alloy transforms from the martensite phase to the more stable, higher strength austenite phase.

Additionally, the occluding devices embodying features of the invention may be formed at least in part of other high strength biocompatible materials such as MP35N alloy, cobalt-chromium alloys, stainless steel, and high strength biocompatible polymeric materials or combinations thereof may be suitable. Biocompatible polymeric materials such as polyethylene terephthalate (PET) Hytrel or a polyamide such as Nylon 6 or ePTFE, may be used. Polymeric materials in combination with metals may be used, such as PET insert molded around NiTi wire. Radiopaque material, such as beryllium sulfate, may also be added to the polymeric material. Furthermore, these materials may include contraceptive drugs (e.g. hormones) which are eluted from the materials to provide contraceptive effect immediately after deployment of the device. The drug(s) may be a spermicidal ingredient or other type of composition.

The occluding devices and placement catheters embodying features of the invention may incorporate coatings which help with insertion and placement of the device. The placement catheters may be coated with a hydrophilic material, such as a PTFE, silicone, or hyrdogel, which reduces friction and allows smooth placement of the occluding device into the fallopian tube. The occluding devices may be coated with a hydrophobic material which promotes tissue growth and placement. A hydrophobic coating will become sticky upon placement to help prevent dislodging or movement. The coating in all cases may be fully or partially biodegradable.

The occluding devices embodying features of the invention may alternatively be placed inside the body without a catheter. Occluding devices may be loaded into a hysteroscope directly and pushed out from an opening in the hysteroscope by a plunger, similar to what is illustrated in FIG. 14F, except a working channel of the hysteroscope being element 74. Additionally a coating may be incorporated on the occluding devices which is hydrophilic to allow ease of insertion.

While particular forms of the invention have been illustrated and described herein, it will be apparent to those skilled in the art that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "sections", "portion", "section", "means", "steps" and words of similar import when used herein shall not be construed as invoking the provisions of 35 U.S.C. .sctn.112(6) unless the following claims expressly use the term "means" followed by a particular function without specific structure or use of the term "step" followed by a particular function without specific action. All patents and patent applications referred to above are hereby incorporated by reference in their entirety. Accordingly, it is not intended that the invention be limited, except as by the appended claims.

The present invention also relates to devices, methods and systems for the occlusion of various passageways of the body including the delivery of therapeutic substances by placement of drugs or drug secreting material on or within such devices. It should be understood that the following examples of occlusion devices also include non-traumatic ends as described above, and as shown in the related figures. The therapeutic substances described herein may also be combined with the devices described above. In the various aspects of occluding body passageways, one object of this invention that is particularly useful is for the occlusion of the fallopian tubes to effect permanent contraception. Although the occlusion of the fallopian tubes will be discussed in detail, it can be appreciated that the devices, methods and systems described herein can easily be adapted to occlude the vas in the male patient, arteries or veins in the nidus of an arterial-venous malformation, patent ductus arteriosis in infants, as well as feeding arteries to cancerous tumors, among other passageways. The invention also provides means for delivering vessel supporting devices such as coronary stents or venous or arterial embolic filters, to the desired location through a steerable system. Although any of these procedures may benefit from the inventions described herein, one particularly useful and immediate benefit for these devices, methods and systems is in the delivery of occlusion devices to the fallopian tubes for contraceptive purposes. At least some of these objectives will be met by the novel inventions, devices, methods and systems described hereinbelow. This invention in some embodiment also provides for delivery of therapeutic substances to desired locations and in advantageous manners.

Those skilled in the art will recognize that various combinations, modifications, and equivalents of the inventions described herein can be used without departing from the scope of these inventions.

The present invention provides devices, methods and systems for the occlusion of various body passageways. It also includes catheter systems for the delivery of embolic devices as well as vascular stents, especially small diameter stents as may be desirable in the coronary or cerebral vasculature. Typically these devices are delivered either by direct placement or by using "over-the-wire" (OTW) designs or techniques. Although OTW designs allow for steerability of the guide wires and delivery catheters, the devices typically must have in inner diameter larger than the removable guide wire with which it is used. The diameter of the guide wire, however, may be too large, even it its smallest functional diameter, to allow for a small enough collapsed profile to transverse through the target passageway. The alternative means of using a pushing device proximal to the collapsed device allows for the device to have a very small collapsed profile since no guide wire needs to pass through it, however such systems may have reduced steerability of the system through the body lumens, particularly distal to the collapsed device. For these reasons and others it would be desirable to have a small diameter system that still allows for steerability of the guide wire while advancing through the body passageways.

Referring now to the examples of the invention shown in the drawings, in accordance with one aspect of this invention, there is provided an expandable lumen occluding and/or substance delivery device 410 that is delivered through a suitable delivery cannula 420 (e.g., a rigid or flexible tube or catheter such as a microcatheter or hypotube). As shown in FIGS. 18A and 18B, the device 410 may be placed in its collapsed configuration and inserted into the lumen of a delivery cannula 420. The delivery cannula 420 comprises a wall 24 that devices a lumen that extends through the cannula 420. A hub 426 may be formed on the proximal end of the delivery cannula 420. After the device 410 has been advanced into the lumen of the cannula, the cannula wall 424 will constrain the device 410 in a relatively collapsed configuration while the device 410 remains inside lumen. In this example, a pusher device 422 comprising an elongate rod 428 and pusher head 430, is useable to facilitate expulsion or release of the device 410 from the delivery cannula 420. Upon exiting the delivery cannula 420, the device 410 resumes its expanded or remembered configuration by the release of a radially expansive force. Alternatively, the device 410 may expand or assume a larger diameter as a result of shape memory (e.g., becoming larger in diameter as a result of temperature change) or other shape altering properties or instrumentalities.

Although the pusher 428 with bulbous pusher head 430 may, in some embodiments, comprise a "pusher wire", it will be understood that the device 410 may be end-loaded into the cannula 420 in the compressed configuration with the pusher 428 in place immediately proximal to the device. When the delivery catheter 420 is placed in the desired location in the body, for example in the fallopian tube, then the cannula 420 may then be withdrawn in the proximal direction while the pusher 428 is held stationary in the longitudinal direction. This has the effect of laying down the expanding occlusive device without actually pushing it forward in the potentially fragile body lumen such as a fallopian tube or tubule in the lung. In this way any injury to the body structure that would otherwise occur by pushing the expanded device forward through the body lumen is avoided. Also, by back-loading the device into the distal end of the delivery catheter, it need not be pushed through the entire length of the catheter. Thus the distal end portion of the delivery cannula 420 may be reinforced, perhaps with slippery substance that makes movement of the device smooth and convenient, and may be reinforced, perhaps with stainless steel wire or the like which would be undesirable for flexibility if the entire length of the catheter had to be so reinforced. In those cases, the "pusher" does not expel the device forward and push it longitudinally thorough the body lumen, but rather stabilizes it as the catheter is withdrawn from over it. Nonetheless, with that understanding, the term "pusher wire" will be used in this patent to describe that device.

In the particular embodiment of the device 410 shown in the drawings, a plurality of first leg segments 415 emanate from a central apex 416. Each first leg segment 415 is joined at an angle with a second leg segment 412, thereby forming a plurality of secondary apices 414, as shown. When the device 410 is expanded or allowed to expand within a body lumen, the second leg segments 412 will contact and exert a constant outward force on the wall of the body lumen in which the device 410 is positioned thereby maintaining in a substantially stationary position within that body lumen. Sometimes at least one of the second leg segments 412 may be formed of thin, relatively rigid material and/or may comprise a projection (e.g., a hook, barb, etc.) that will lodge in the lumen wall to secure the device 410 in place.

It will be appreciated that, although the device 410 may comprise a single unit as shown in the figures, the invention includes systems or embodiments wherein a plurality of these single unit devices 410 are aligned or positioned adjacent to each other to form a multi-unit occluding system or structure within a body lumen. In such embodiments, the aligned or adjacently positioned single unit devices 410 may optionally be joined or connected to one. another to form a unitary structure. In this regard, it will be appreciated that two or more of the devices 410 (separate or conjoined) may be loaded into the lumen of the delivery cannula 420 an expelled from the distal end 425 of the delivery cannula 420 by the pusher 422. Alternatively, a plurality of the devices 410 may be loaded into and expelled from the delivery cannula 420, one at a time, thereby implanting a plurality of the devices 410 in series within a body lumen.

In some embodiments, the configuration of the device may be modified from that shown in the figures to a generally tubular shape that is expandable and collapsible, as with a stent. Devices of this general nature are described in U.S. Pat. No. 6,096,052 (Callister et al.) and U.S. Pat. No. 6,432,116 (Callister et al.), the complete disclosures of which are incorporated herein as if set forth in full.

The device 410 may be configured, constructed or contain materials that support or facilitate tissue ingrowth. As used herein, the term tissue ingrowth includes but is not limited to cell mulitiplication and/or or growth resulting in tissue formation into, onto, or surrounding a particular region and/or into, onto or surrounding an obstructive device. This may be epithelization, scar formation, or other cell growth or multiplication. For example, the leg portions 412,415 and/or matrix 418 may incorporate materials that promote epithelialization, endothelialization, granulation or other proliferative or tissue growth response within the body to create a more effective occlusion of the passageway or to result in a more secure attachment of the occlusion device to the walls of the body lumen. For instance, polyester fibers may be attached to the device 410 such that tissue ingrowth into and around the device will form a plug and thereby occlude the lumen in which the device is implanted. In some embodiments, a volitionally deployable wall abrading projection (e.g., a flare or projection) may be provided on the distal portion of the cannula 420 and/or on the device 410 to abrade or denude the epithelial layer of the fallopian tube FT or other body lumen in which the device 410 is implanted, thereby enhancing the tissue ingrowth response. Such volitionally deployable wall abrading projection could both be deployed when entering the body lumen and/or when deploying the device 410.

Additionally, as described in detail herebelow, substances such as therapeutic agents, drugs, (e.g., contraceptive hormones, spermicidal agents, spermatogenesis inhibitors, antimicrobials, antibiotics, antifungals, chemotherapeutic agents, biologics, etc.) or biological factors (VEGf, FGF, etc.) may be incorporated on or within the device in order to bring about some desired effect (e.g., to accelerate tissue ingrowth, prevent/treat infection, cause drug-induced contraception for at least a sufficient period of time to allow the implanted lumen occluding device to become fully functional, treat a disease or disorder in the adjacent tissue, etc). When the implantable device of this invention is used to block the lumen of a fallopian tube, vas deferens or other body lumen for the purpose of deterring pregnancy, the lumen blocking efficacy of the device (and thus its reliability as a contraceptive measure) may not become maximized for several weeks or months after the initial implantation of the device 410 as such amount of time may be required for the implanted device 410 to become fully epithelialized or for other tissue ingrowth to become complete. In such instances, a quantity of a contraceptive agent and/or spermicidal agent may be incorporated on or in the device so as to provide for drug-induced contraception for a period of time that is at least sufficient to allow the lumen blocking efficacy of the device to become maximized. Examples of specific substances (e.g., drugs, therapeutic agents, biological factors, etc.) that may be incorporated into or onto the device 410 of this invention or any other lumen occluding device are described herebelow.

FIGS. 19A-19B show a system for OTW delivery of the lumen occluding and/or substance delivery device 410. This system generally comprises the lumen occluding and/or substance delivery device 410, a delivery cannula 420 as described above and a modified pusher device 428a that has a guidewire lumen extending longitudinally therethrough such that a guidewire 432 may pass through the lumen of the pusher device 428a, through the lumen occluding and/or substance delivery device 410 and through the lumen of the delivery cannula 420, as shown in FIG. 19A. Alternatively, and not shown in the figures, the pusher head 430a may have a groove therein through which the guidewire 432 may slide so that it will be located longitudinally side-by side with the pusher 429a. Optionally, the guidewire 432 may have a distal portion 434 that is more flexible than the proximal portion of the guidewire and/or is otherwise deflectable, flexible or steerable. In operation, the guidewire 432 may be advanced into a desired body lumen (e.g., a fallopian tube) into which it is desired to implant the lumen occluding and/or substance delivery device 410. Thereafter, the delivery cannula 420 having the device 410 and pusher 428a within its lumen may be advanced over the previously inserted guidwire to a location where the distal end of the delivery cannula 420 is adjacent to the location where it is desired to implant the device 410. Thereafter, the pusher 428a may be advanced over the guidewire 432 such that the enlarged distal end 430a of the pusher 428a will expel the lumen occluding and/or substance delivery device 410 out of the distal end of the delivery cannula 420. The device 410 will then self expand within the body lumen such that the second leg segments 412 of the device engage the wall of the body lumen. Thereafter, the delivery cannula 420, pusher 428a and guidewire 432 may be removed, leaving the device 410 implanted within the body lumen.

Figure 20:
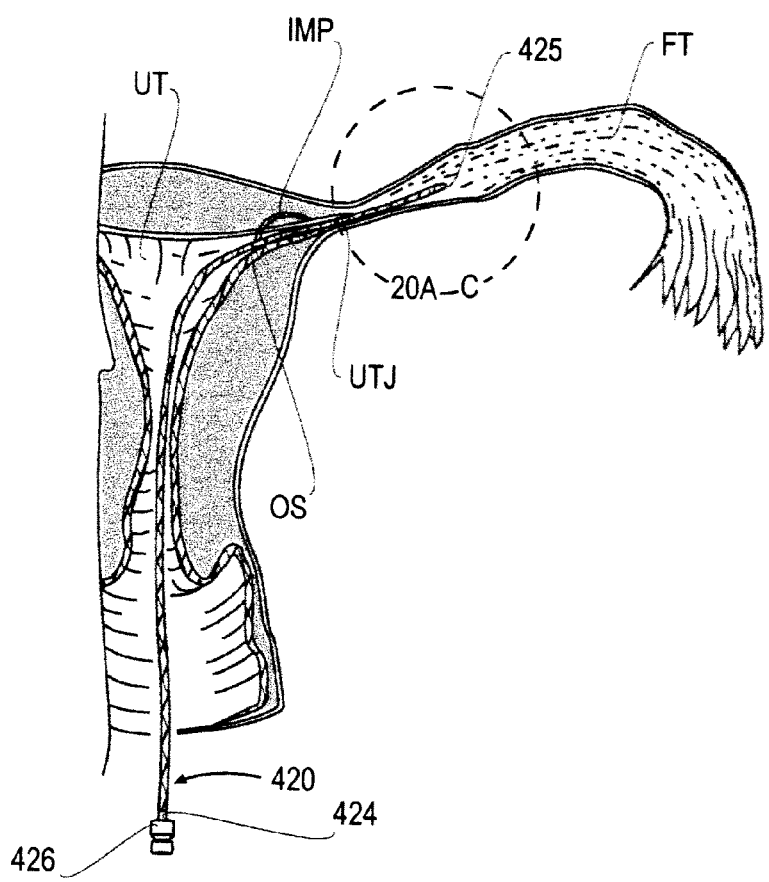
FIG. 20 is a sectional showing of the uterus and left fallopian tube of a human patient having the over-the-wire system of FIGS. 19A and 19B inserted into the left fallopian tube.
Figure 20A:
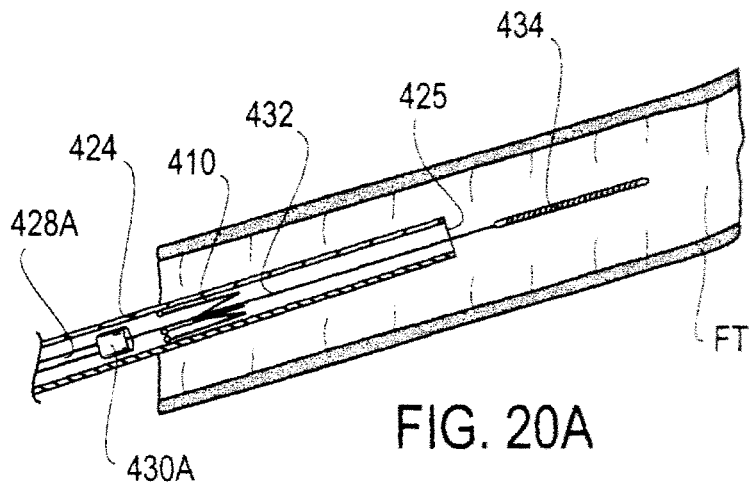
FIGS. 20A-20C show three steps in a procedure wherein the system shown in FIG. 20 is used to implant a lumen occluding/substance delivery device in the patient's left fallopian tube; the implant includes an exemplary embodiment of non-traumatic ends on the implant.
Figure 20B:
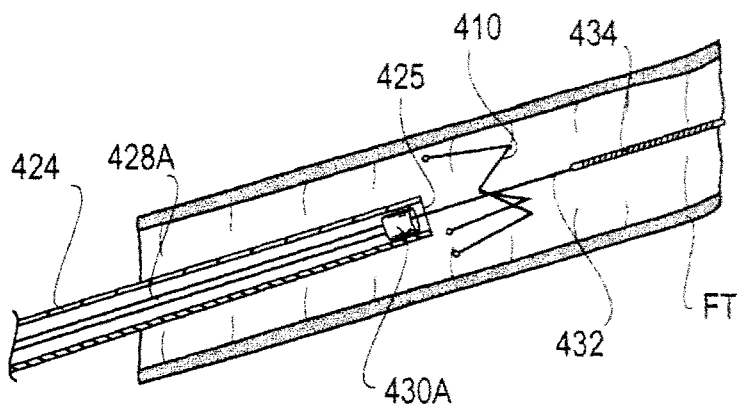
Figure 20C:
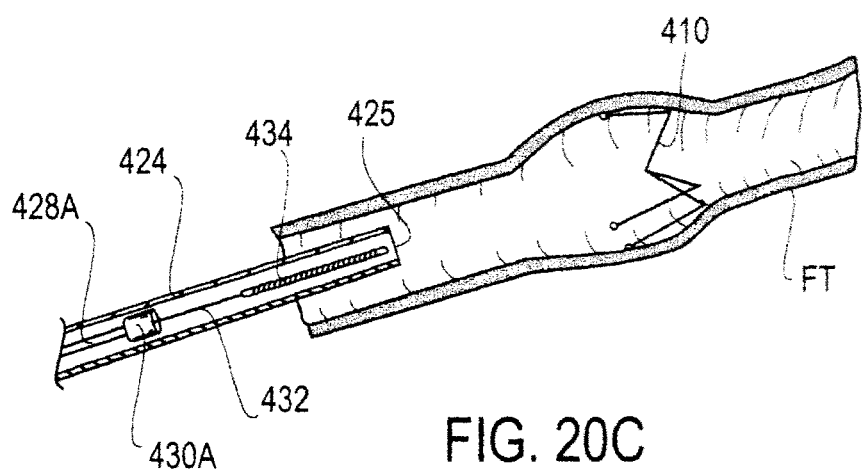

FIGS. 20-20C show a specific procedure in which the OTW system shown in FIGS. 19A-19C is used to implant a lumen occluding and/or substance delivery device 410 within a fallopian tube. Initially, the guidewire 432 is advanced through the uterus UT and into the fallopian tube FT. The delivery catheter 420 (with the collapsed device 410 and pusher 428a positioned therein) is advanced over the guidewire 432, as seen in FIG. 20A. Thereafter, as shown in FIG. 20B, the pusher 428a is advanced over the guidewire 432 such that the enlarged distal end 430a of the pusher 428a pushes the device 410 out of the distal end 425 of the delivery cannula 420. Upon exiting the distal end 425 of the delivery cannula 420, the device 410 self expands to its expanded configuration whereby the second leg segments 412 of the device 410 are urged against the wall of the fallopian tube FT, thereby holding the device 410 in a fixed position, as shown in FIG. 20C. The delivery cannula 420, pusher 428a and guidewire 432 are then withdrawn through the uterus UT and removed, leaving the device 410 implanted within the fallopian tube FT. Following implantation, tissue will ingrow into the device 410 to cause complete occlusion of the fallopian tube FT. At least during the period of time during which such tissue ingrowth is occurring, the device 410 may elute a substance (e.g., a contraceptive or spermicidal substance) in an amount that causes a desired therapeutic effect (e.g., contraception or spermicide) in the patient. Optionally, the device 410 may include a matrix 418, as described above, to facilitate the desired tissue ingrowth and/or to deliver the desired substance.

If more than one device 410 is to be implanted within the subject's body, there is no need to remove the delivery cannula 420 to deliver the additional devices. For instance, if devices 410 are to be implanted in both fallopian tubes FT, the delivery catheter 420 may initially contain two devices 410, one for each fallopian tube FT. In such an instance, the physician may insert the delivery catheter 420 through the uterus of the patient, and deliver one device to the first of two fallopian tubes FT, and, after delivery of the first device 410, the physician may then insert the delivery catheter 420 into the other fallopian tube 420 and deploy the second device 410 into the other fallopian tube FT without having to withdraw the delivery cannula 420 from the uterus UT. This has the advantage of speeding the overall procedure time since there is no need to remove and replace a delivery cannula 420 for each fallopian tube FT. Additionally, overall costs for the procedure are reduced since only one delivery cannula 420 and one pusher 428a are used to place two devices 410. Alternatively, the present invention also allows for the lumen occluding and/or substance delivery device 410 to be advanced through the entire length of the delivery cannula 420. In such an instance, the delivery cannula 420 is advanced to the location where the device 410 is to be placed. The guide wire 432 may aid in positioning the delivery cannula 420. Following acceptable placement of the delivery cannula 420, the guide wire 432 may be removed from the delivery cannula 420 and the first occlusion device 410 may then be placed in a collapsed configuration and loaded into the lumen of the cannlua 420 through its proximal end. After the device 410 has been located within lumen of the delivery cannula 420, a standard pusher 438 (see FIGS. 18A and 18B) may be used to advance the device 410 through the length of the delivery cannula 420 and out of its distal end 425. The device 410 will then expand and become implanted within the lumen of the fallopian tube FT in the manner described hereabove.

In accordance with yet another aspect of this invention, it will be appreciated that the enlarged pusher head 430 or 430a could actually be mounted on the guidewire 432 at a location proximal to the device 410 such that, as the guidewire 432 is advanced in the distal direction (or as the cannula 420 is withdrawn in the proximal direction) the pusher head 430 or 430a will push the device 410 along with it.

One major advantage to the type of system shown in FIGS. 20A-20B is that the entire system may be steerable, since the distal portion 434 of the guide wire 432 may be constructed to be torqued or steered through the body passageways to its desired location. A small hole may be formed in the central apex 416 of the device 410 and the guidewire 432 may pass through that hole. Thus, such torquing the guide wire 432 may have no significant effect on the device 410 since even in its collapsed state within the delivery cannula 420 there is still a small hole through the device 410 through which the guide wire 432 passes.

The distal portion 434 of the guide wire 432 may be flexible and may incorporate a conventional spring tip or, alternatively, it may be made of or incorporate a plastic or Teflon coating to prevent any snagging of any attached fibers on the occlusion device. Additionally, the device 410 may be positioned on a reduced diameter segment of the guidewire 432 and such reduced diameter segment may be longer than the device 410. This will permit a limited amount of axial movement of the guide wire 432, either proximally or distally, to further aid in the bendability and/or steerability of the system. Delivery cannula 420 may thus be able to provide either more or less support for the guide wire support, depending on the circumstances and the tortuosity of the vasculature or passageway being navigated. In such embodiments wherein the guide wire 432 is axially moveable over a limited range but not completely removeable may allow the use of a steerable guide wire 432 having a relatively large diameter distal portion in combination with a low profile delivery cannula 420 (e.g., a delivery cannula 420 that has a diameter that is the same as or even smaller than the diameter of the distal portion of the guide wire 432). It will be appreciated by those of skill in the art that the device 410 may be self-expanding, or it may be pressure expanded (e.g., plastically deformable) through the use of a balloon catheter or the like. In some self-expanding embodiments, the device 410 may assume its expanded configuration as a result of temperature shape memory or release of compression, or any other appropriate means. As the device 410 assumes its expanded configuration as shown in FIG. 20C, it may expand across the body lumen in which it is positioned and assume a configuration wherein any guidewire passage hole or opening formed in the device 410 will be large enough to allow the guidewire 432 to be retracted through the expanded device 410 and back into the lumen of the delivery cannula 420 for withdrawal, leaving the device 410 in place.

Figure 25:
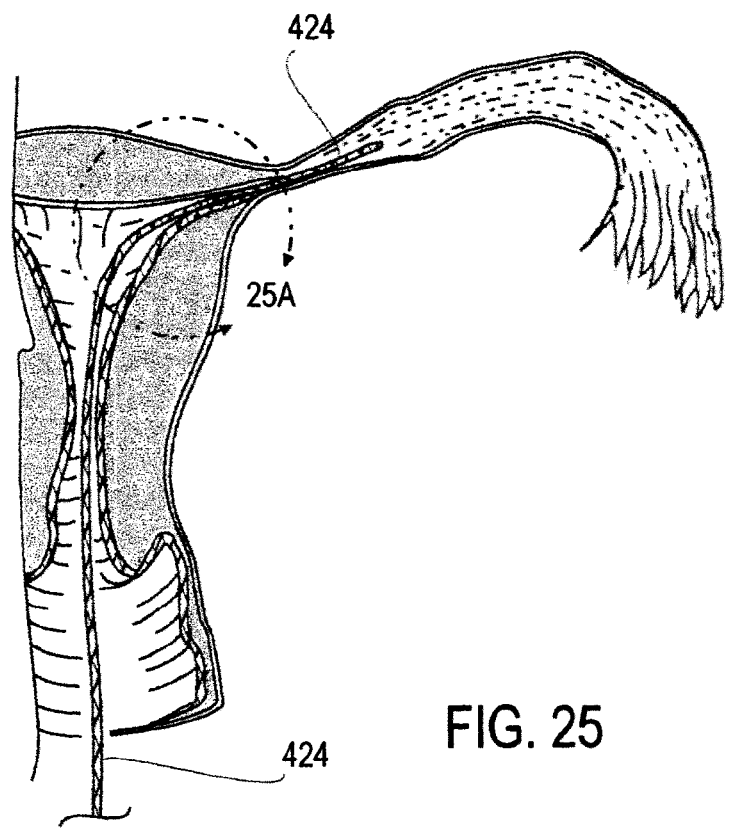
FIG. 25 is a sectional showing of the uterus and left fallopian tube of a human patient having a hysteroscope and a delivery system according to the present invention inserted into the left fallopian tube.
Figure 25A:
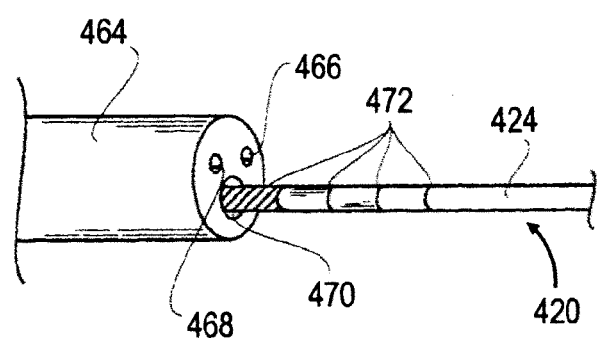
FIG. 25A is an enlarged view of the distal end of the hysteroscope and adjacent portion of segment 25A of FIG. 25, showing advancement of the delivery catheter out of a working channel of the hysteroscope.

FIGS. 25 and 25A show an example of a procedure wherein a hysteroscope 464 is used to view and/or facilitate implantation of a lumen occluding and/or substance delivery device 410. The hysteroscope 464 comprises an elongate, flexible device having a lumen or working channel 470, a light emission lens or port 468 and an image receiving lens or port 466. Initially, the hysteroscope 464 is advanced through the uterus UT and into the proximal fallopian tube FT, as shown. The delivery cannula 420 is then advanced through the working channel 470 of the hysteroscope 464. The physician may view, through the hysteroscope 464, the advancement of the delivery cannula 420 out of the distal end of the hysteroscope 464. Length indicating colored zone(s) and/or markings 472 may be provided at specific locations on the delivery cannula 420 to indicate the length delivery cannula 420 that has been advanced from the distal end of the hysteroscope 464. Thus, the physician may advance the cannula 420 until he or she sees a specific colored zone or other length marking 472 which indicates that the cannula 420 has been advanced to the desired depth or location within the fallopian tube FT. length marking(s) 472 may be formed at locations on the delivery cannula 420 to indicate to the physician through the hysteroscope 464 that the distal end of the delivery cannula 420 has reached a desired implantation site distal to the fallopian tube ostium OS, typically within the intramural portion IMP of the fallopian tube FT or within the utero-tubal UTJ. In some cases the device 410 may be implanted elsewhere in the fallopian tube FT, such as in the isthmic region of the fallopian tube FT, distal to the isthmic region, or even in or near the ampulla region of the fallopian tube. In some embodiments, three separate markings 472 (e.g., 3 different colored zones or visible markings such as ruler type hash marks) the physician to selectively advance the delivery cannula 420 to one of several identified implantation sites (e.g., in the isthmus, between or spanning the transition between the isthmus and ampulla and in the ampulla. An alternative to visual means of determining the position or depth of insertion of the delivery cannula 420 is the use of ultrasound, electronic or image based guidance. In embodiments where ultrasound is used to determine the position of the delivery cannula 420, one or more echogenic marker(s) may be placed on the tip of or elsewhere on the delivery cannula 420 and/or on the implantable device 410 within the delivery cannula 420 to facilitate ultrasonic imaging and proper placement of the device 410 under ultrasonic guidance. Optionally, a physical barrier may be located on the delivery cannula 420 to prevent over-insertion.

Another means of placement for the device is under fluoroscopic guidance. In this case, one or more radiopaque marker(s) may be located on the tip of or elsewhere on the delivery cannula 420 and/or on the implantable device 410 within the delivery cannula 420 to facilitate positioning of the delivery cannula 420 and/or device 410 under fluoroscopy.

The lumen occluding and/or substance delivery device 410 may deliver (e.g., elute) substance(s) (e.g., drugs, therapeutic agents, biologics, proteins, spermicides, biological factors, cell preparations, friendly microbes, etc.) for some period of time following implantation into the body. In this regard, the device 410 may be of the configuration and structure shown in the figures and described hereabove, may be configured as a drug eluting substance such as fibers contained in a tubular structure, or may be of any other suitable configuration or structure. The rate and/or amount of substance delivered from the implanted device may be designed or controlled, in accordance with known drug delivery technology, to both control dosage (e.g. concentration in the uterus, fallopian tube, lung, tumor or other tissue, organ or anatomical structure), the location of delivery (e.g. systemic, local, topical, directed downstream in a feeding artery, etc.) and the time period over which the drug or other substance would be eluded or otherwise delivered by the implanted device. Also, in some aspects, the delivery of a substance from the device 410 may be responsive to a physical condition or presence/flow of a body fluid in the patient, such as a substance that is eluted by the device 410 and/or carried from the device 410 to another location as a result of the presence of certain conditions, such as different times in the menstrual cycle, or different blood chemistry conditions during the diurnal cycle, or different conditions as a result of physical or medical conditions such as the presence of certain biological factors, the blood pressure presented, the blood flow encountered, or the like.

The substance that is to be eluted or delivered from the implanted intraluminal device may be placed on or in the device 410 in various ways, examples of which are shown in FIGS. 21A-23B. For example, the device 410 or some portion thereof may be consist of or comprise a hollow member (e.g., a tube or hollow fiber) having a lumen or inner cavity wherein the substance is contained and the substance may then elute from that hollow member by diffusion through a wall or portion of the hollow member, by seepage or transport out of an aperture or opening formed in the hollow member, or by any other suitable means. FIG. 21 shows an example of the device 410 wherein a substance delivering matrix 418 is disposed on the device 410. This matrix 418 acts not only acts as a matrix (e.g., scaffold, form or support structure) for tissue ingrowth but also is coated with, impregnated with or contains a substance, such that the substance will elute from or otherwise be delivered from the matrix 418 following implantation of the device 410. FIG. 21A shows an example wherein the matrix 418 or a portion thereof is formed of a hollow member 418a (e.g., a hollow fiber) that has a lumen 438 wherein the substance is initially contained and a wall 436 through which the substance will diffuse or otherwise pass, thereby resulting in a release or elution of the substance from the hollow member 418a. FIG. 21B shows another example wherein the matrix 418 or a portion thereof is formed of a hollow member 418B that has a wall 440 and a lumen of inner cavity that opens through an opening 442 formed in one end or elsewhere in the wall 440 of the hollow member 418b such that substance contained in the lumen or inner cavity of the hollow member 418b will pass out of the opening 442, thereby resulting in a release or elution of the substance from the hollow member 418a. Each hollow member 418a, 418b may be extruded or otherwise formed such that its inner diameter, wall thickness and/or outlet opening size controls the rate at which the drug or other substance will be eluted from or delivered by the device 410. The amount of or depth to which the drug or other substance is loaded into each hollow member 418a, 418b could control the dispersal of the drug over time (i.e. more drug in the hollow fiber will provide for a longer period of time over which the drug will be delivered). It will be appreciated that, additionally or alternatively, the hollow members 418a, 418b shown in FIGS. 21A and 21B could be used to form all or portions of the leg members 412 and/or 415 such that substance will elute from or be delivered by the leg members 412 and/or 415 in addition to or as an alternative to elution or delivery of substance from the matrix 418.

Figures 22, 22A, 22B, 22C:
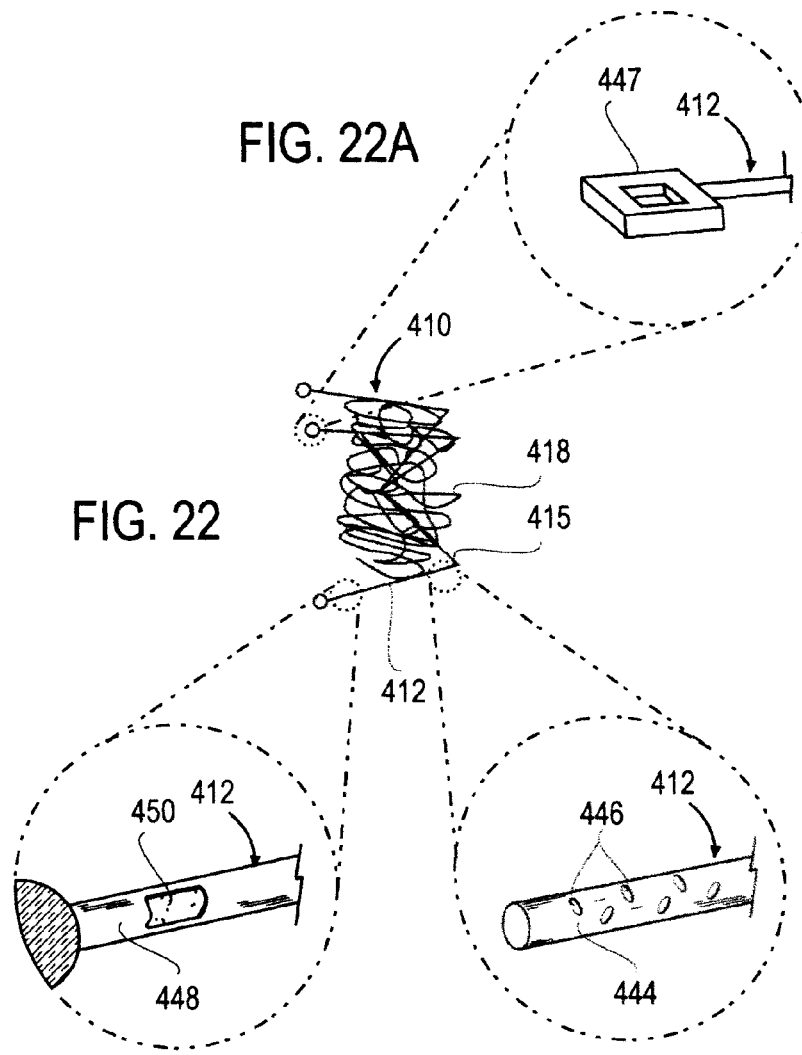
FIG. 22 is an enlarged perspective view of a lumen occluding/substance delivery device (with non-traumatic ends) of the present invention having an optional substance delivery and/or ingrowth supporting matrix thereon and wherein portions of the device are constructed to carry out controlled delivery of a substance following its implantation within the body of a patient.
FIG. 22A is an enlarged view of a portion of the device of FIG. 22 illustrating one way in which the device may be constructed to deliver a substance following its implantation within the body of a patient.
FIG. 22B is an enlarged view of a portion of the device of FIG. 22 illustrating another way in which the device may be constructed to deliver a substance following its implantation within the body of a patient.
FIG. 22C is an enlarged view of a portion of the device of FIG. 22 illustrating yet another way in which the device may be constructed to deliver a substance following its implantation within the body of a patient.

FIGS. 22-22C show other examples wherein all or portion(s) of the leg member(s) 412 and/or 415 are constructed to contain and deliver a drug or other substance. In some embodiments, all or portion(s) of the leg members 412 and/or 415 may be hollow, cellular, permeable or cavernous such that they may contain a drug or other substance (see FIGS. 22B and 22C) or one or more reservoir members may be attached to the device 410 to contain the drug or other substance (see FIG. 22A). The drug or other substance may then diffuse, leak, transport or otherwise pass out of the reservoir through semipermeable membrane(s) or openings.

For example, as shown in FIG. 22A, a semipermiable reservoir member 447 which contains the drug or other substance may be attached to the end of one or more leg(s) 412 such that the drug or substance will diffuse through the wall of the reservoir member 447 thereby delivering a therapeutically effective dose of the drug or substance to the subject over a desired period of time. The reservoir member 447 may or may not be removable from the implanted device 410 and, in some embodiments, the reservoir member 447 may be replaceable by another full reservoir member 447 in situ while the device 410 remains in place. For example, in applications where the device 410 is implanted within a fallopian tube FT for the purpose of contraception, the reservoir member 447 may be removed and/or replaced at a later date via a hysteroscope 464 and a suitable removal device such as a gripping device or forceps that may be passable through a working channel 470 of the scope 464. Alternatively, the reservoir member 447 may be refillable, for example by a syringe.

FIG. 22B shows an example wherein a portion 448 of a leg member 412 is hollow and contains the drug or substance and wherein a semipermeable window 450 is formed of material through which the drug or other substance will diffuse such that therapeutically effective dose of the drug or substance will be delivered to the subject over a desired period of time.

FIG. 22C shows an example wherein a portion 444 of a leg member 412 is hollow and contains the drug or substance and wherein a plurality of small holes 446 are formed in that portion of the leg 412 such that the drug or other substance will seep or otherwise flow out of the holes and a therapeutically effective dose of the drug or substance will be delivered to the subject over a desired period of time.

Additionally or alternatively, the substance may comprise or may be contained in particles (e.g., granules, beads, vesicles, blisters, bubbles, capsules, lyposomes, microcapsules, etc.) that are disposed on (e.g., adhered or affixed to)

some portion of the device 410 such that the substance will be released is from the particles after the device 410 has been implanted.

Figure 23:
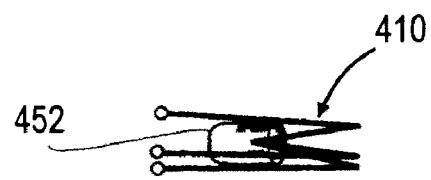
FIG. 23 is a side view of a lumen occluding/substance delivery device (with non-traumatic ends) according to the present invention, disposed in a collapsed configuration and having a substance delivery reservoir thereon.
Figure 23A:
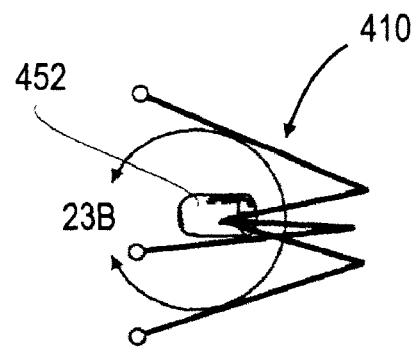
FIG. 23A is a side view of the device of FIG. 23 disposed in an expanded configuration.
Figure 23B:
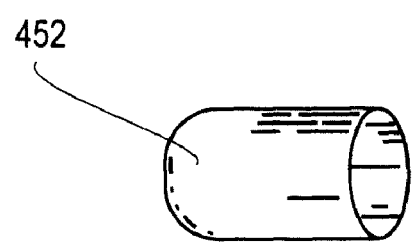
FIG. 23B is an enlarged perspective view of the substance delivery reservoir of the device of FIGS. 23 and 23A.

FIGS. 23-23B show another example, wherein a substance delivering implant 452, such as a pellet or capsule, is separate from or may be attached to and/or associated with the lumen occluding and/or substance delivery device 410.

For example, in embodiments where the device 410 is implanted in a fallopian tube FT for contraceptive purposes, a contraceptive drug delivering implant 452 may be implanted proximally to, within, or distally to the device 410. The matrix of the pellet, in some embodiments, may be biodegradable (e.g., formed of polylactic acid, polyglycolic acid, etc.) such that after a desired or predetermined period of time, the pellet would dissolve and be gone. Methods for making substance delivering pellets or implants are previously known in the art including those described in U.S. Pat. Nos. 3,625,214; 3,991,750; 5,855,915 and 6,306,914, the entireties of which are expressly incorporated herein by reference.

It is to be appreciated that the drug or other substance may be incorporated into any portion or element of the device 410 in any suitable way. For example, the drug or substance may be mixed in to a material (e.g., a plastic) that flows, dissolves, melts, oozes or otherwise passes out of the device 410 following implantation. In such embodiments, the molecules of the drug or substance may be sized so as to migrate or pass between polymer chains of the plastic such that the drug or substance will leach or pass out of the plastic over a desired time period. In certain embodiments, the drug or substance may make up or be incorporated into a coating that is extruded or applied over all or a portion of the material located in or on the device, such that the drug or substance will elute or pass out of the coating at a desired rate or over a desired time period. In certain embodiments the drug or substance may make up or may be incorporated in a coating that is applied to all or a portion of the device 410 (e.g., the leg members 412 and/or 415 may be formed of a material such as self expanding nickel-titanium alloy or other metal and may be coated with a coating that consists of or contains the drug or substance) such that the drug or substance will elute or pass out of that coating at a desired rate or over a desired time period. In certain embodiments, one or more holes, indentations or other texture may be drilled or otherwise formed in the leg members 412 and/or 415 or the optional matrix 418 or other portion(s) of the device 410 and the desired drug or substance may be placed in the hole(s), indentation(s) or other texture such that the drug or substance will elute or pass out of the hole(s), indentation(s) or other texture over a desired time period. The diameter(s) and/or depth(s) of the hole(s), indentation(s) or other texture may be selected to control the rate and time over which the drug or substance will elute or otherwise pass from the device. In certain embodiments the substance may be responsive to the physiological conditions and thereby control the delivery of the substance in response to those conditions. For example, where the substance is released for contraceptive purposes within the fallopian tubes, the release of the substance may be controlled to some extent by the menstrual cycle of the patient. Certain well known biochemical conditions prevail within the uterus and fallopian tubes at the time and shortly after the release of the egg from the ovaries (referred to here as ovulation). A pellet of spermicidal substance or other similar contraceptive substance may be coated with a substance that is soluble in response to the biochemical conditions that prevail at the time of ovulation, but relatively insoluble in the biochemical conditions that prevail in the uterus and fallopian tubes at other times. This would result in the release of the substance primarily at the time of ovulation, and thus result in a long lasting contraceptive pellet that enhances contraception at precisely the time when it will be effective. Another example of the release of the substance in response to physiological conditions would be where a greater amount of substance is released in response to increased blood flow, as in a chemotherapeutic agent located in a feeding artery to a tumor. As the blood flow decreases, smaller amounts of the chemotherapeutic substance is released, resulting in decreased systemic effects as the blood flow to the tumor is cut off. Responses to blood pressure, diurnal cycles, and the like can also be engineered in accordance with this invention.

Figure 24:
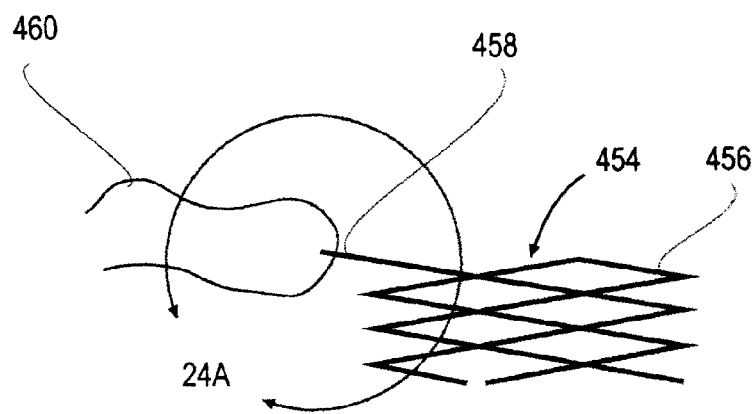
FIG. 24 is a perspective view of another embodiment of a lumen occluding/substance delivery device according to the present invention having an optional visualization member thereon.
Figure 24A:
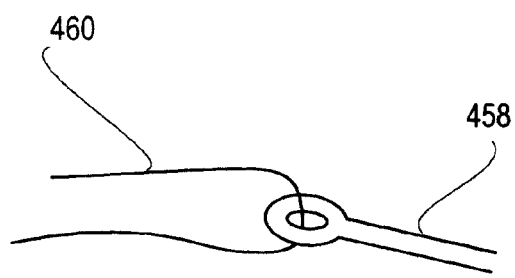
FIG. 24A is an enlarged view of a portion of the device of FIG. 24.

As shown in FIGS. 24 and 24A, the invention also provides an implantable lumen occluding and/or substance delivering device 454 that further comprises a flag or marker 460 that unravels or extends out of the fallopian tube and into the uterus for visual confirmation to indicate which fallopian tube has a device 454 in it. In this particular non-limiting example, the device 454 comprises a mesh body 456 that is designed to facilitate tissue ingrowth and occlude of a fallopian tube or other body lumen in which it is implanted. An arm 458 extends from the body 456 and the marker 460 is attached to the arm 458, as shown. Optionally, this flag or marker 460 and/or the body 456 of the device 454 can contain a substance (e.g., contraceptive drug, antifungal, antibiotic, agent for treatment of STD such as pelvic inflammatory disease, spermicidal agent, etc.) as described above. Also, optionally, this flag or marker 460 may be dissolvable or biodegradable and/or retrievable and removable at a later date, such through an endoscope or hysteroscope as described above. In embodiments, where the flag or marker 460 or any other component of the device is removable from the body, that component may contain substance(s), such as copper, that are desirable for only for short term implantation.

The substance eluting implantable devices 410, 454 of the present invention may be useable in various applications. For example, as described above, in applications where the device 410, 454 is implanted in a fallopian tube FT or elsewhere in the female genitourinary tract for the purpose of blocking egg migration or implantation, the device 410, 454 may additionally elute or deliver a female contraceptive agent or spermicidal agent to deter pregnancy, at least for some initial period of time following implantation of the intraluminal device. Any effective contraceptive or spermicidal agent may be used, in amounts that result in the desired therapeutic effect of avoiding pregnancy.

Specific examples of contraceptive agents that may be used include; the contraceptive hormone contained in the Norplant system (e.g., a synthetic progestin, namely, levonorgestrel having the molecular formula (d (–)-13-beta-ethyl-17-alpha-ethinyl-17-beta-hydroxygon-4-en-3-one) and a molecular weight of 312.45 and/or various other contraceptive hormone preparations including but not limited to medroxyprogesterone acetate, norethisterone enanthate, progestogen, levonorgestrel, levonorgestrel (as progestogen), ethinyl estradiol (as estrogen), norgestrel (as progestogen), levonorgestrel in combination with ethinyl estradiol, Norethisterone enanthate, norgestrel in combination with ethinyl estradiol, quinacrine, etc. Quinacrine is not a hormone. Rather, quinacrine is an agent which may be used to cause chemical, non-surgical female sterilization. When a quinacrine hydrocholoride pellet is inserted directly into the uterus, the guinacrine liquefies and flows into the fallopian tubes, causing permanent scarring. Although recorded failure rates and persistent side effects related to quinacrine sterilization have been low, controversy has developed around quinacrine's long-term safety, efficacy, and link to upper genital tract infections. However, direct placement of quinacrine into the fallopian tube in combination with or as part of a lumen blocking implantable device of this invention may permit the use or relatively low levels of quinacrine which would facilitate a local effect within the fallopian tube without untoward systemic toxicity.

In applications where the device 410 is implanted within a fallopian tube FT to cause contraception, the device 410 may deliver a contraceptive agent in an amount that a) causes an effect on the uterine tissue (e.g., endometrium) such that eggs will not become implanted within the uterus UT and/or b) causes cessation of ovulation. Typically, the dose of contraceptive substance delivered to cause cessation of ovulation is higher than the dose delivered to cause non-implantation of eggs in the endometrium. For example, the device 10 may deliver from about 10 micrograms to about 70 micrograms of levonorgestrel (d (−)-13-beta-ethyl-17-alpha-ethinyl-17-beta-hydroxygon-4-en-3-one). Dosages of levonorgestrel within the lower portion of this dosage range (e.g., from about 10 micrograms per day to about 30 micrograms per day) may be used to cause non-implantation of eggs in the endometrium while dosages within the higher portion of that dosage range (e.g., from about 30 micrograms per day to about 70 micrograms per day) may be used to cause cessation of ovulation. The dosages may vary however and this invention is not limited to any specific dosage or any specific agent. Indeed, the optimal dosage of a particular contraceptive agent to be delivered from the device 10 may depend on various factors, such as the age of the patient, the specific location at which the device 10 is implanted in the fallopian tube Fr, whether devices 10 are implanted on only one or both fallopian tubes FT, etc.

Specific examples of specific spermicidal agents that may be used include but are not limited to nonoxynol-9, octoxynol-9, menfegol, benzalkonium chloride and N-docasanol.

Also, in any application where infection or microbial infestation is a concern, the device may elute or deliver antimicrobial agent(s) (e.g., microbicidal agents, antibiotics, antiviral agent(s), anti paracyte agent(s), etc.) Specific examples of antimicrobial agents that may be eluted or delivered from the implanted device include but are not limited to: Acyclovir; Amantadine; Aminoglycosides (e.g., Amikacin, Gentamicin and Tobramycin); Amoxicillin; Amoxicillin/Clavulanate; Amphotericin B; Ampicillin; Ampicillin/sulbactam; Atovaquone; Azithromycin; Cefazolin; Cefepime; Cefotaxime; Cefotetan; Cefpodoxime; Ceftazidime; Ceftizoxime; Ceftriaxone; Cefuroxime; Cephalexin; Chloramphenicol; Clotrimazole; Ciprofloxacin; Clarithromycin; Clindamycin; Dapsone; Dicloxacillin; Doxycycline; Erythromycin; Fluconazole; Foscarnet; Ganciclovir; Gatifloxacin; Imipenem/Cilastatin; Isoniazid, Itraconazole+(Sporanox.RTM.); Ketoconazole; Metronidazole; Nafcillin; Nafcillin; Nystatin; Penicillin; Penicillin G; Pentamidine; Piperacillin/Tazobactam; Rifampin; Quinupristin-Dalfopristin; Ticarcillin/clavulanate; Trimethoprim/Sulfamethoxazole; Valacyclovir; Vancomycin; Mafenide; Silver Sulfadiazine; Mupirocin; Nystatin; Triamcinolone/Nystatin; Clotrimazole/Betamethasone; Clotrimazole; Ketoconazole; Butoconazole; Miconazole; Tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent HIV or other retroviruses from replicating in the cells; genetically engineered or naturally occurring antibodies that combat pathogens such as anti-viral antibodies genetically engineered from plants known as "Plantibodies," agents which change the condition of the tissue to make it hostile to the pathogen (such as substances which alter vaginal pH (e.g., Buffer Gel and Acidform) or bacteria which cause the production of hydrogen peroxide within the vagina (e.g., lactobacillus).

Also, in some applications, a substance eluting implantable device may be placed in a body lumen (e.g., blood vessel, bronchus, hepatic duct, common bile duct, pancreatic duct, etc.) near a tumor and the device may deliver one or more anti-tumor agents to treat the tumor. Specific examples of anti-tumor agents that may be used in this invention include but are not limited to: alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), Antitumor antibiotics and other compounds that act by binding or intercalating DNA and preventing RNA synthesis (e.g., doxorubicin, daunorubicin, epirubicin, idarubicin, mitomycin-C and bleomycin)Plant (vinca) alkaloids and other anti-tumor agents derived from plants (e.g., vincristine and vinblastine), Steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide (Thalomid), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000)), biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Figures 26, 26A:
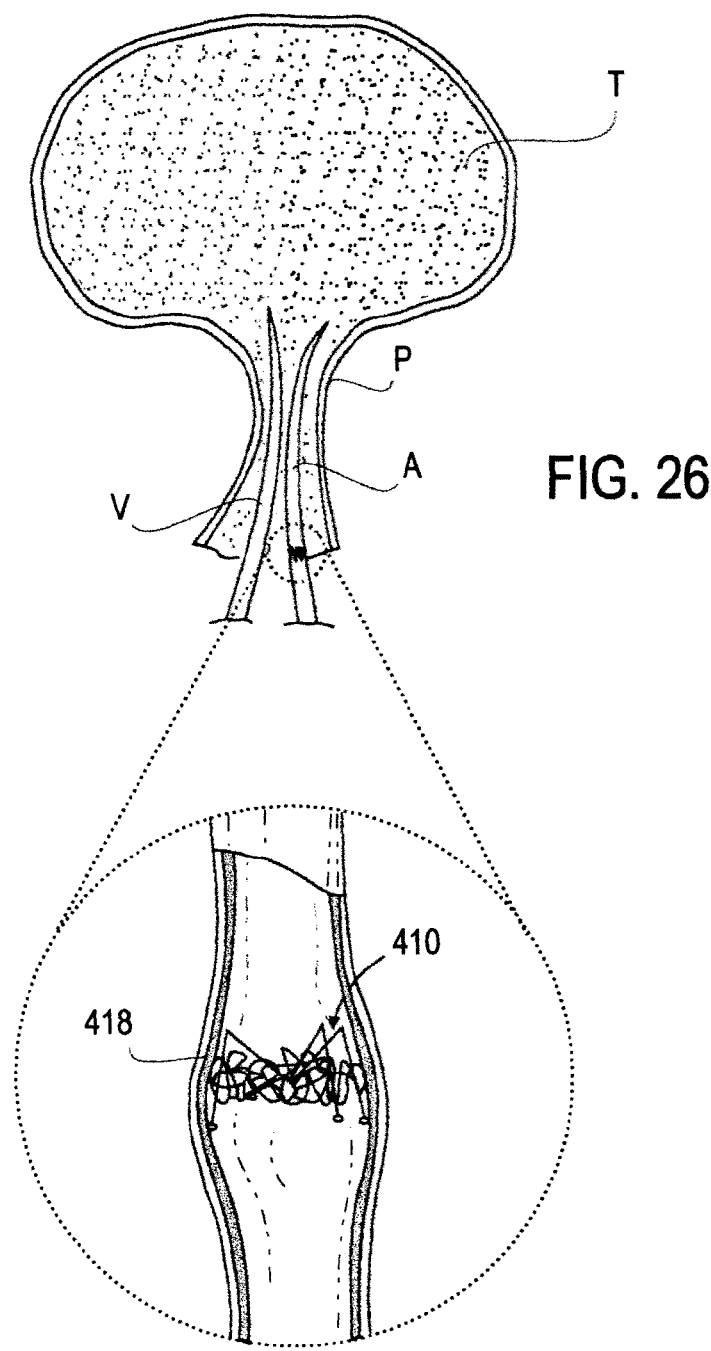
FIG. 26A is a sectional view of a vessel showing the manner in which implantation of a lumen occluding/substance delivery device of the present invention may block the flow and/or to deliver an antineoplastic or antitumor substance to a tumor shown in FIG. 26.

In some embodiments the lumen occluding and/or substance delivering device 410, 454 may be used for antitumor applications. In the example shown in FIGS. 26 and 26A, a tumor T has a peduncle P through which and artery A and vein V run. A lumen occluding and/or substance delivering device 410 of the present invention is implanted in the artery A to occlude the artery A thereby cutting of blood flow to the tumor and/or to deliver an antineoplastic or antitumor substance to the tumor T. In some of these applications, the implanted device 410 may continue to allow some flow of blood or other body fluid through the body lumen in which it is positioned and into the tumor for at least an initial period of time following implantation of the device (e.g., until tissue ingrowth into the device 410 closes off the lumen of the blood vessel or other body lumen). In this way, the antitumor substance eluted or delivered by the device 410 will be carried into the tumor T for some desired period of time following implantation. Thereafter, cellular ingrowth into the device 410 causes a progressive and complete occlusion of the artery A after the desired dose of antitumor substance has been delivered to the tumor T. This blockage of blood flow to the tumor T may further serve to inhibit or kill some or all of any remaining tumor cells that have not been killed by the antitumor drug. The release of the drug may be controlled based on the rate of blood flow through the feeding vessel. As the artery A occludes over time, less total amount of the drug will be released into the bloodstream and thus there will be less systemic effects of the chemotherapeutic agent which will generally result in less dramatic side effects. On the other hand, the concentration of the antitumor substance will generally be slightly more concentrated in the blood based on the reduced flow, resulting in a more concentrated but more localized therapeutic effect on the tumor T.

Figure 27:
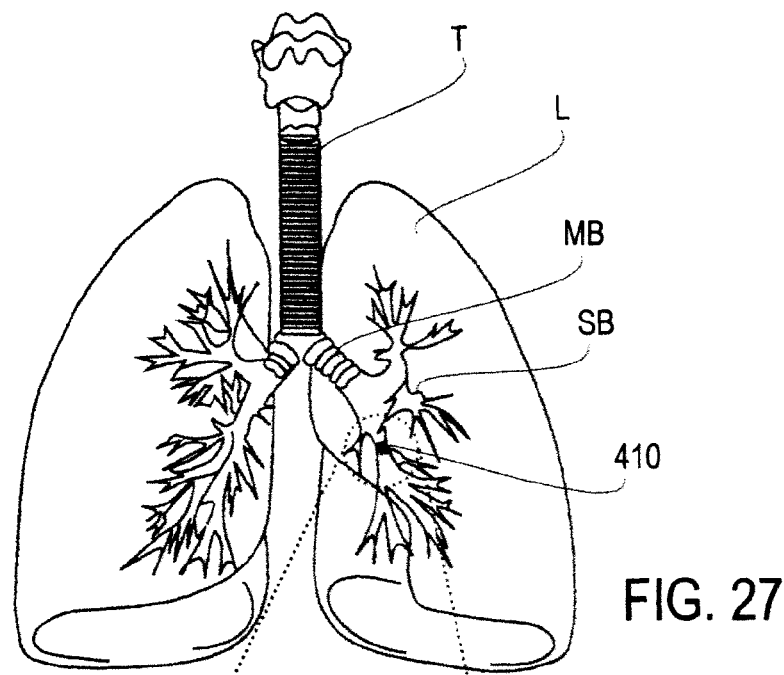
FIG. 27 is a view of the lungs of a patient into which an occlusive delivery device of the invention has been inserted.
Figure 27A:
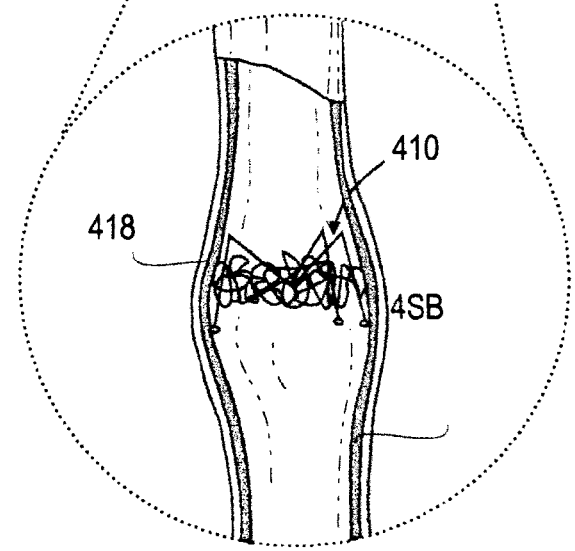
FIG. 27A is an expanded, partially cut-away view of the portion of FIG. 27 indicated by the dashed circle.
Figure 27B:
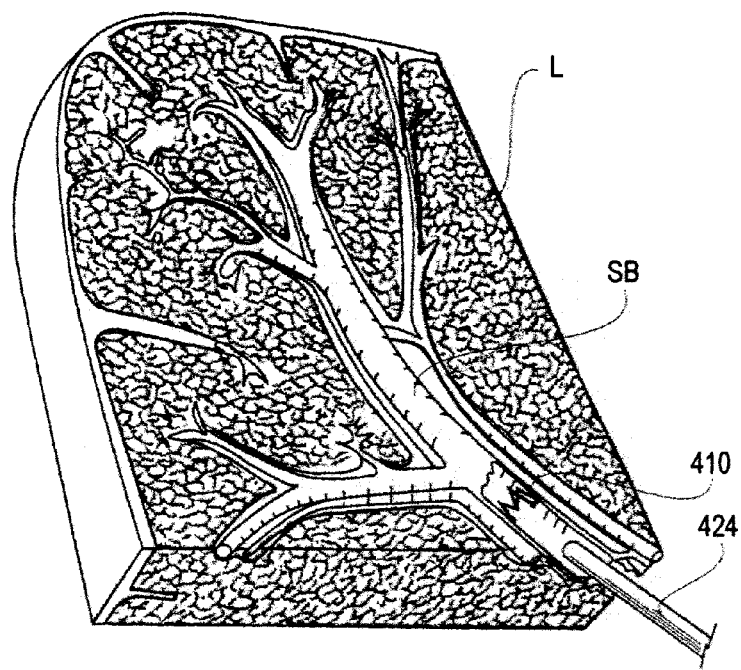
FIG. 27B is a cut-away view of a portion of a patient's lung showing the delivery catheter and the occlusive device in place.

In yet another example of an application of this invention shown in FIGS. 27-27B, the implantable intraluminal device 410 is implanted into a lung L to block air flow to a portion of the lung L. As seen in FIG. 27, the trachea T is bifurcated into right and left mainstem bronchi MB. Each mainstem bronchus MB then branches into a number of secondary bronchi SB. In the particular non-limiting example shown, the device 410 is implanted into a secondary bronchus SB that leads into the lower lobe of the left lung L. Following implantation, the device 410 may cause instant or progressive full occlusion of the secondary bronchus SB, so as to prevent air from entering the diseased lobe or region of lung parenchyma that receives air through that secondary bronchus SB. Such leakage or disease may result from, for example, a ruptured emphysematous bleb, traumatic lung puncture or iatrogenic lung rupture. In other cases the device 410 may be constructed so as not to substantially block airflow through the bronchus and possibly even to perform a scaffolding or stenting function which holds the lumen of the bronchus open. In either type of device, a drug or substance may be eluted or delivered by the device into the adjacent pulmonary tissue. For example, in cases where the device has been implanted to close off flow to a punctured area of the lung, the device may elute an antibiotic or other agent (e.g., a bronchodilator, mucolytic agent, expectorant, etc.) to locally deter or treat any infection or other condition present or developing in the lung tissue. In cases where the device 410 is implanted in a bronchus to treat emphysema or chronic obstructive pulmonary disease, the device may elute a therapeutic agent that is effective to treat that underlying condition or its symptoms.

Some examples of drugs that may be eluted from the device for the purpose of treating such lung diseases include but are not limited to: antimicrobial substances (examples of which are listed hereabove); corticosteroids such as beclomethasone (Vanceril, Beclovent), triamcinolone (Azmacort), flunisolide (Aerobid), fluticasone (Flovent), budesonide (Pulmicort), dexamethasone, prednisone, prednisolone, methylprednisolone (Medrol, SoluMedrol, DepoMedrol), methylprednisolone (Depo-Medrol), hydrocortisone (SoluCortef), methylprednisolone (SoluMedrol); Mediator-release inhibitors or cromones such as, cromolyn sodium (Intal), nedocromil sodium (Tilade); anti-leukotriene drugs such as leukotriene-receptor antagonists (e.g., zafirlukast (Accolate)), leukotriene-synthesis inhibitors (e.g., zileuton (Zyflo)) and other anti-leukotrienes (e.g., montelukast (Singulair)), mucolytic agents and expectorants (e.g., guifenisn); bronchodilator drugs such as beta-adrenergic agonists (e.g., epinephrine (Primatene), isoproterenol (Isuprel), isoetharine (Bronkosol), metaproterenol (Alupent, Metaprel), albuterol (Proventil, Ventolin), terbutaline (Bricanyl, Brethine), bitolterol (Tornalate), pirbuterol (Maxair), salmeterol (Serevent), Methyl xanthines (e.g., caffeine, theophylline, aminophylline and oxtriphylline (Choledyl)) and anticholinergics (e.g., atropine, ipratropium bromide (Atrovent).

It will be appreciated by those skilled in the art that various modifications, additions, deletions, combinations and changes may be made to the examples described hereabove and shown in the drawings, without departing from the intended spirit and scope of this invention. All such reasonable modifications, additions, deletions, combinations and changes are included in this disclosure.

What is claimed is:

1. An occluding device for a patient's body lumen, comprising:
    a. a first spider segment having a first expansive element having a first end secured to a central location in the occluding member and a non-traumatic end radially spaced from the first end when in an expanded configuration and, at least one additional expansive element having a first end secured to the central location in the occluding member and a non-traumatic end radially spaced from the central location in the expanded configuration; and
    b. a second spider segment axially spaced from the first spider segment, having a first expansive element having a first end secured to the central location in the occluding member and a non-traumatic end radially spaced from the first end when in an expanded configuration and at least one additional expansive element having a first end secured to the central location in the occluding member and a non-traumatic end radially spaced from the central location in the expanded configuration;
    wherein each non-traumatic end is a separate, discrete mesh pad with fibers attached thereto, and each separate, discrete mesh pad is bonded onto a respective expansive element and configured to face an adjacent wall of the body lumen when in the expanded configuration in the body lumen.

2. The occluding device of claim 1 wherein a connecting member interconnects the first spider segment with an adjacent spider segment.

3. The occluding device of claim 2 wherein the connecting member is straight.

4. The occluding device of claim 3 wherein at least one connecting member extends between each spider segment and an adjacent spider segment.

5. The device of claim 3 wherein the first, second and intermediate spider segments are axially aligned.

6. The device of claim 3 wherein the spider segments are connected to adjacent spider segments by a connecting member which extends axially along the central location within the occluding member.

7. The device of claim 1 additionally comprising at least one extension member having a first extension member end and a free end, the first extension member end secured to the central location.

8. The device of claim 7 wherein the extension member comprises a coil.

9. The device of claim 7 wherein the free end is non-traumatic.

10. The occluding device of claim 1 further comprising at least one hydrogel element, which upon insertion into the patient expands to block the lumen.

11. The occluding device of claim 10 wherein the hydrogel element is porous to allow tissue ingrowth.

12. The occluding device of claim 10 wherein the hydrogel element carries a contraceptive drug.

13. The occluding device of claim 10 wherein the hydrogel element is between the first and second spider segments.

14. The occluding device of claim 2 wherein the adjacent spider segment is the second spider segment.

15. The occluding device of claim 2 wherein the connecting member is curved.

16. The occluding device of claim 1 including at least one intermediate spider segment which is axially disposed between the first and second spider segments and which has: a first expansive element having a first end secured to the central location in the occluding member and a non-traumatic end radially spaced from the first end when in an expanded configuration and at least one additional expansive element having a first end secured to the central location in the occluding member and a non-traumatic end radially spaced from the first end when in the expanded configuration.

17. The device of claim 1 additionally comprising fibers inter-disposed between the first and second spider segments.

18. The device of claim 1 additionally comprising a therapeutic substance on at least one expansive element.

19. The device of claim 1 additionally comprising a membrane inter-disposed between at least one of the spider segments.

20. The occluding device of claim 1 wherein each of the mesh pads comprise a molded part bonded onto the respective expansive element.

21. An occluding device for a patient's body lumen, comprising:
   a. a first spider segment having a first expansive element having a first end secured to a central location in the occluding member and a non-traumatic end radially spaced from the central location when in an expanded configuration and, at least one additional expansive element having a first end secured to the central location in the occluding member and a non-traumatic end radially spaced from the central location in the expanded configuration; and
   b. a second spider segment axially spaced from the first spider segment, having a first expansive element having a first end secured to the central location in the occluding member and a non-traumatic end radially spaced from the central location when in an expanded configuration and at least one additional expansive element having a first end secured to the central location in the occluding member and a non-traumatic end radially spaced from the central location in the expanded configuration;
   wherein each non-traumatic end is a separate, discrete mesh pad with fibers attached thereto, and each separate, discrete mesh pad is bonded onto a respective expansive element and configured to face an adjacent wall of the body lumen when in the expanded configuration in the body lumen.

22. The occluding device of claim 21 wherein each of the mesh pads comprise a molded part bonded onto the respective expansive element.

23. The occluding device of claim 21 wherein a connecting member interconnects the first spider segment with the second spider segment.

24. The occluding device of claim 21 further comprising a membrane inter-disposed between at least one of the first and second spider segments.

* * * * *